US012655397B2

(12) United States Patent
Tran et al.

(10) Patent No.: US 12,655,397 B2
(45) Date of Patent: Jun. 16, 2026

(54) VIRAL EXTRACTION FROM CELL CULTURE

(71) Applicant: National Research Council of Canada, Ottawa (CA)

(72) Inventors: Hue Tran, Calgary (CA); Matthew Coffey, Calgary (CA); Allison Hagerman, Calgary (CA); Robert Voyer, Lachine (CA); Krishna Raj Tiwari, Mont-Royal (CA); Jyoti Latawa, Mont-Royal (CA); Mehul Patel, Dollard des Ormeaux (CA); Allan Matte, Dollard des Ormeaux (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 19/273,808

(22) Filed: Jul. 18, 2025

(65) Prior Publication Data

US 2025/0346868 A1    Nov. 13, 2025

Related U.S. Application Data

(63) Continuation of application No. PCT/IB2024/053862, filed on Apr. 19, 2024.

(60) Provisional application No. 63/461,216, filed on Apr. 21, 2023.

(51) Int. Cl.
 *C12N 7/00*    (2006.01)
(52) U.S. Cl.
 CPC ...... *C12N 7/00* (2013.01); *C12N 2720/12251* (2013.01)
(58) Field of Classification Search
 None
 See application file for complete search history.

(56) References Cited

U.S. PATENT DOCUMENTS

2006/0088869 A1* 4/2006 Coffey ..................... C12N 7/00
435/5

FOREIGN PATENT DOCUMENTS

| WO | WO-9911791 A2 * | 3/1999 | ............. C07K 14/52 |
| WO | 03093463 A1 | 11/2003 | |
| WO | 2006042414 A1 | 4/2006 | |

OTHER PUBLICATIONS

Eagle's Minimum Essential Medium (MEM) with Earle's Salt. Retrieved from: https://resources.rndsystems.com/pdfs/datasheets/ M36450.pdf on Oct. 2, 2025. Published Jun. 23, 2024. 2-page printout (Year: 2024).*
International Application No. PCT/IB2024/053862, "International Search Report and Written Opinion", Jun. 25, 2024, 9 pages.
"Optimization of midstream cell lysis and virus filtration steps in an adenovirus purification process." (2018).
Moleirinho, Mafalda G. et al. "Clinical-grade Oncolytic Adenovirus Purification using Polysorbate 20 as an Alternative for Cell Lysis." Current Gene Therapy 18 (2018): 366-374.
Elveborg, Simon et al. "Methods of Inactivation of Highly Pathogenic Viruses for Molecular, Serology or Vaccine Development Purposes." Pathogens 11 (2022): n. pag.
European Search Report issued on Mar. 20, 2026 in EP application No. 24792262.8-1111.

* cited by examiner

*Primary Examiner* — Benjamin P Blumel
*Assistant Examiner* — Jeffrey Mark Sifford
(74) *Attorney, Agent, or Firm* — Honigman LLP

(57) ABSTRACT

Provided herein are methods of producing virus from a culture of host cells. The methods include providing a culture of host cells which has been infected by the virus; contacting the host cells with a first buffer comprising a detergent and incubating the host cells in the presence of the first buffer for a first period of time thereby producing a cell lysate; contacting the cell lysate with a second buffer comprising an endonuclease for a second period of time to degrade the host cell nucleic acids; and collecting the virus.

28 Claims, 3 Drawing Sheets

Specification includes a Sequence Listing.

Post-Clarification

—●—Tween® 20, 10 U/mL   – ● –Tween® 20, 20 U/mL   -----Triton™, 10 U/mL 1 x O/N @ 4°C —●—Tween® 20, 10 U/mL   – ● –Tween® 20, 20 U/mL   ------Triton™, 10 U/mL

SEQUENCE LISTING

```
Sequence total quantity: 30
SEQ ID NO: 1                moltype = DNA  length = 1416
FEATURE                     Location/Qualifiers
source                      1..1416
                            mol_type = genomic DNA
                            organism = Reovirus
SEQUENCE: 1
gctattggtc ggatggatcc tcgcctacgt gaagaagtag tacggctgat aatcgcatta   60
acgagtgata atggagcatc actgtcaaaa gggcttgaat caagggtctc ggcgctcgag  120
aagacgtctc aaatacactc tgatactatc ctccggatca cccagggact cgatgatgca  180
aacaaacgaa tcatcgctct tgagcaaagt cgggatgact tggttgcatc agtcagtgat  240
gctcaacttg caatctccag attggaaagc tctatcggag ccctccaaac agttgtcaat  300
ggacttgatt cgagtgttac ccagttgggt gctcgagtgg gacaacttga gacaggactt  360
gcagagctac gcgttgatca cgacaatctc gttgcgagag tggatactgc agaacgtaac  420
attggatcat tgaccactga gctatcaact ctgacgttac gagtaacatc catacaagcg  480
gatttcgaat ctaggatatc cacgttagag cgcacggcgg tcactagcgc gggagctccc  540
ctctcaatcc gtaataaccg tatgaccatg ggattaaatg atggactcac gttgtcaggg  600
aataatctcg ccatccgatt gccaggaaat acgggtctga atattcaaaa tggtggactt  660
cagtttcgat ttaatactga tcaattccag atagttaata ataacttgac tctcaagacg  720
actgtgtttg attctatcaa ctcaaggata gggcaactg agcaaagtta cgtggcgtcg  780
gcagtgactc ccttgagatt aaacagtagc acgaaggtgc tggatatgct aatagacagt  840
tcaacacttg aaattaattc tagtggacag ctaactgtta gatcgacatc cccgaatttg  900
aggtatccga tagctgatgt tagcggcggt atcggaatga gtccaaatta taggtttagg  960
cagagcatgt ggataggaat tgtctcctat tctggtagtg ggctgaattg agggtacag  1020
gtgaactccg acatttttat tgtagatgat tacatacata tatgtcttcc agcttttgac  1080
ggtttctcta tagctgacgg tggagatcta tcgttgaact ttgttaccgg attgttacca  1140
ccgttactta caggagacac tgagcccgct tttcataatg acgtggtcac atatggagca  1200
cagactgtag ctatagggtt gtcgtcgggt ggtgcgcgtc agtatatgag taagaatctg  1260
tgggtggagc agtggcagga tggagtactt cggttacgtg ttgaggggg tggctcaatt  1320
acgcactcaa acagtaagtg gcctgccatg accgtttcgt acccgcgtag tttcacgtga  1380
ggatcagacc accccgcggc actggggcat ttcatc                           1416

SEQ ID NO: 2                moltype = DNA  length = 1331
FEATURE                     Location/Qualifiers
source                      1..1331
                            mol_type = genomic DNA
                            organism = Reovirus
SEQUENCE: 2
gctattcgct ggtcagttat ggctcgcgct gcgttcctat tcaagactgt tgggtttggt   60
ggtctgcaaa atgtgccaat taacgacgaa ctatcttcac atctactccg agctggtaat  120
tcaccatggc agttaacaca gtttttagac tggataagcc ttgggagggg tttagctaca  180
tcggctctcg ttccgacggc tgggtcaaga tactatcaaa tgagttgcct tctaagtggc  240
actctccaga ttccgttccg tcctaaccac cgatggggag acattaggtt cttacgctta  300
gtgtggtcag ctcctactct cgatggatta gtcgtagctc caccacaagt tttggctcag  360
cccgctttgc aagcacaggc agatcgagtg tacgactgcg atgattatcc atttctagcg  420
cgtgatccaa gattcaaaca tcgggtgtat cagcaattga gtgctgtaac tctacttaac  480
ttgacaggtt ttggcccgat ttcctacgtt cgagtggatg aagatatgtg gagtggagat  540
gtgaaccagc ttctcatgaa ctatttcggg cacacgtttg cagagattgc atacacattg  600
tgtcaagcct cggctaatag gccttgggaa tatgacggta catatgctag gatgactcag  660
attgtgttat ccttgttctg gctatcgtat gtcggtgtaa ttcatcagca gaatacgtat  720
cggacattct attttcagtg taatcggcga ggtgacgccg ctgaggtgtg gattctttct  780
tgttcgttga accattccgc acaaattaga ccgggtaatc gtagcttatt cgttatgcca  840
actagcccag attggaacat ggacgtcaat ttgatcctga gttcaacgtt gagtgtcgcgt  900
ttgtgttcgg gttcacagct gccactgatt gacaataatt cagtacctgc agtgtcgcgt  960
aacatccatg gctggactgg tagagctggt aaccaattgc atgggttcca ggtgagacga  1020
atggtgactg aattttgtga caggttgaga cgcgatggtg tcatgaccca agctcagcag  1080
aatcaagttg aagcgttggc agatacagact caacagttta agagggacaa gctcgaaacg  1140
tgggcgagag aagacgatca atataatcag gctcatccca actccacaat gttccgtacg  1200
aaaccattta cgaatgcgca atggggacga ggtaatacgg gggcgactag tgccgcgatt  1260
gcagcccta tctgatcgtc ttggagtgag ggggtccccc cacacacctc acgactgacc  1320
acacattcat c                                                       1331

SEQ ID NO: 3                moltype = DNA  length = 1198
FEATURE                     Location/Qualifiers
source                      1..1198
                            mol_type = genomic DNA
                            organism = Reovirus
SEQUENCE: 3
```

```
gctaaagtca cgcctgtcgt cgtcactatg gcttcctcac tcagagctgc gatctccaag    60
atcaagaggg atgacgtcgg tcagcaagtt tgtcctaatt atgtcatgct gcggtcctct   120
gtcacaacaa aggtggtacg aaatgtggtt gagtatcaaa ttcgtacggg cggattcttt   180
tcgtgcttag ctatgctaag gccactccag tacgctaagc gtgagcgttt gcttggtcag   240
aggaatctgg aacgtatatc gactagggat atccttcaga ctcgtgattt acactcacta   300
tgtatgccaa ctcctgatgc gccaatgtct aatcatcaag catccaccat gagagagctg   360
atttgcagtt acttcaaggt cgatcatgcg gatgggttga aatatatacc catggatgag   420
agatactctc cgtcatcact tgccagattg tttaccatgg gcatggctgg gctgcacatt   480
accactgagc catcttataa gcgtgttccg attatgcact tagctgcgga cttggactgt   540
atgacgctgg ctctacctta catgattacg cttgatggtg atactgtggt tcctgtcgct   600
ccaacactgt cagcggaaca gcttctggac gacggactca aaggattagc atgcatggat   660
atctcctatg gatgtgaggt ggacgcgaat agccggccgg ctggtgatca gagtatggac   720
tcttcacgct gcatcaacga gttgtattgc gaggagacag cagaagccat ctgtgtgctt   780
aagacatgcc ttgtgttaaa ttgcatgcag tttaaacttg agatggatga cctagcacat   840
aacgctgctg agctggacaa gatacagatg atgatacect tcagtgagcg tgttttagg    900
atggcctcgt cctttgcgac tattgatgcc cagtgtttta ggtttgcgt gatgatgaag    960
gataaaaatc tgaaaataga tatgcgtgaa acgacgagac tgtggactcg ttcagcatca  1020
gatgattctg tggccacgtc atctttaagt atttccctgg accggggtcg atgggtggcg  1080
gctgacgcca gtgatgctag actgctggtt tttccgattc gcgtgtaatg ggtgagtgag  1140
ctgatgtggt cgccaagaca tgtgccggtg tcttggtggt gggtgacgcc taatcatc    1198
```

SEQ ID NO: 4                moltype = DNA  length = 1196
FEATURE                     Location/Qualifiers
source                      1..1196
                            mol_type = genomic DNA
                            organism = Reovirus
SEQUENCE: 4

```
gctattttg cctcttccca gacgttgtcg caatggaggt gtgcttgccc aacggtcatc    60
aggtcgtgga cttaattaac aacgctttg aaggtcgtgt atcaatctac agcgcgcaag   120
agggatggga caaaacaatc tcagcacagc cagatatgat ggtatgtgt ggcgccgtcg   180
tttgcatgca ttgtctaggt gttgttggat ctctacaacg caagctgaag catttgcctc   240
accatagatg taatcaacag atccgtcatc aggattacgt cgatgtacag ttcgcagacc   300
gtgttactgc tcactggaag cggggtatgc tgtccttcgt tgcgcagatg cacgagatga   360
tgaatgacgt gtcgccagat gacctggatc gtgtgcgtac tgagggaggt tcactagtca   420
agctgaaccg gcttcaggtt gacccaaatt caatgtttag atcaatacac tcaagttgga   480
cagatccttt gcaggtggtg gacgaccttg cactaagct ggatcagtac tggacagcct    540
taaacctgat gatcgactca tccgacttga tacccaactt tatgatgaga gacccatcac   600
acgcgttcaa tggtgtgaaa ctgaagggag atgctcgtca aacccaattc tccaggactt   660
ttgattcgag atcgagtttg gaatggggtg tgatggttta tgattactct gagctggatc   720
atgatccatc gaagggccgt gcttacgaa aggaattggt gacgccagct cgagatttcg    780
gtcactttgg attatcccat tattctaggg cgactacccc aatccttgga aagatgccgg   840
ccgtattctc aggaatgttg actgggaact gtaaaatgta tccattcatt aaaggaacgg   900
ctaagctgaa gacagtgcgc aagctagtg aggcagtcaa tcatgcttgg ggtgtcgaa    960
agattagata tgctcttggg ccaggtggca tgacgggatg gtacaatagg actatgcaac  1020
aggcccccat tgtgctaact cctgctgctc tcacaatgtt cccagatacc atcaagtttg  1080
gggatttgaa ttatccagtg atgattggcg atccgatgat tcttggctaa acacccccat  1140
cttcacagcg ccgggcttga ccaacctggt gtgacgtggg acaggcttca ttcatc       1196
```

SEQ ID NO: 5                moltype = DNA  length = 2304
FEATURE                     Location/Qualifiers
source                      1..2304
                            mol_type = genomic DNA
                            organism = Reovirus
SEQUENCE: 5

```
gctattcgcg gtcatggctt acatcgcagt tcctgcggtg gtggattcac gttcgagtga    60
ggctattgga ctgctagaat cgtttggagt agacgctggg gctgacgcga atgacgtttc   120
atatcaagat catgactatg tgttggatca gttacagtac atgttagatg gatatagaggc   180
tggtgacgtt atcgatgcac tcgtccacaa gaattggtta catcactctg tctattgctt   240
gttgccaccc aaaagtcaac tattagagta ttggaaaagt aatccttcag cgataccgga   300
caacgttgat cgtcggcttc gtaaacgact aatgctaaag aaagatctca ggaaagatga   360
tgaatacaat cagctagcgc gtgctttcaa gatatcggat gtctacgcac ctctcatctc   420
atccacgacg tcaccgatga caatgataca gaacttgaat cgaggcgaga tcgtgtacac   480
cacgacggac agggtaatag gggctagaat cttgttatat gctcctagaa agtactatgc   540
gtcaactctg tcatttacta tgactaagtg catcattccg tttgataaag aggtgggtcg   600
tgttcctcac tctcgattta atgttggcac atttccgtca attgctaccc cgaaatgttt   660
tgtcatgagt ggggttgata ttgagtccat cccaaatgaa tttatcaagt tgttttacca   720
gcgcgtcaag agtgttcacg ctaacatact aaatgacata tctcctcaga tcgtctctga   780
catgataaac agaaagcgtc tgcgcgttca tactccatca gatcgtcgag ccgcgcagtt   840
gatgcatttg cctaccatg ttaaacgagg agcgtctcac gtcgacgttt acaaggtgga     900
tgttgtagac atgttgttcg aggtagtgga tgtggccgat gggttgcgca acgtatctag   960
gaaactaact atgcataccg ttcctgtatg tattcttgaa atgttgggta ttgagattgc  1020
ggactattgc attcgtcaag aggatggaat gctcacagat tggttcctac tttttaaccat  1080
gctatctgat ggcttgactg atagaaggac gcattgtcaa tacttgatta atccgtcaag  1140
tgtgcctcct gatgtgatac ttaacatctc aattactgga tttataaata gacatacaat  1200
cgatgtcatg cctgacatat atgacttcgt taaacccatt ggcgctgtgc tgcctaaggg  1260
atcatttaaa tcaacaatta tgagagttct tgattcaata tcaatattag gaatccaaat  1320
catgccgcgc gcgcatgtag ttgactcaga tgaggtgggc gagcaaatgg agcctacgtt  1380
tgagcaggcg gttatggaga tatacaaagg gattgctggc gttgactcgc tggatgatct  1440
catcaagtgg gtgttgaact cggatctcat tccgcatgat gacaggcttg gtcaattatt  1500
```

-continued

```
tcaagcgttt ttgcctctcg caaaggactt attagctcca atggccagaa agttttatga   1560
taactcaatg agtgagggta gattgctaac attctctcat gccgacagtg agttgctgaa   1620
cgcaaattat tttggtcatt tattgcgact aaaaatacca tatattacag aggttaatct   1680
gatgattcgc aagaatcgtg agggtggaga gctatttcag cttgtgttat cttatctata   1740
taaaatgtat gctactagcg cgcagcctaa atggtttgga tcattattgc gattgttaat   1800
atgtccctgg ttacatatgg agaaattaat aggagaagca gacccggcat ctacgtcggc   1860
tgaaattggg tggcatatcc ctcgtgaaca gctgatgcaa gatggatggt gtggatgtga   1920
agacggattc attccctatg ttagcatacg tgcgccaaga ctggttatag aggagttgat   1980
ggagaagaac tggggccaat atcatgccca agttattgtc actgatcagc ttgtcgtagg   2040
cgaaccgcgg agggtatctg ctaaggctgt gatcaagggt aaccacttac cagttaagtt   2100
agtttcacga tttgcatgtt tcacattgac ggcgaagtat gagatgaggc tttcgtgcgg   2160
ccatagcact ggacgtggag ctgcatacag tgcgagacta gctttccgat ctgacttggc   2220
gtgatccgtg acatgcgtag tgtgacacct gctcctaggt caatgggggt aggggcgggg   2280
ctaagactac gtacgcgctt catc                                          2304
```

SEQ ID NO: 6　　　　　　moltype = DNA　length = 2204
FEATURE　　　　　　　　　Location/Qualifiers
source　　　　　　　　　1..2204
　　　　　　　　　　　　mol_type = genomic DNA
　　　　　　　　　　　　organism = Reovirus
SEQUENCE: 6

```
ggctaatctg ctgaccgtta ctctgcaaag atggggaacg cttcctctat cgttcagacg   60
atcaacgtca ctggagatgg caatgtattt aaaccatcag ctgaaacttc atctaccgct   120
gtaccatcgt taagcttatc acctggaatg ctgaatcccg gaggggtacc atggattgct   180
gttggagatg agacatctgt gacttcacca ggcgcattac gtcgaatgac gtcaaaggac   240
atcccggaca cggcaataat caacacagac aattcatcag gcgccgtgcc aagcgaatca   300
gccttggtgc cctacatcga tgagccgctg gtagtggtta cagagcatgc tattaccaac   360
ttcaccaaag ctgagatggc acttgaattc aatcgtgagt tccttgacaa gatgcgtgtg   420
ctgtcagtgt caccaaaata ttcggatctt ctgacctatg ttgactgcta cgtcggtgtg   480
tctgctcgtc aggctttaaa caattttcag aaacaagtgc ctgtgattac acctactagg   540
cagacgatgt atgtcgactc gatacaagcg gccttgaaag ctttagaaaa gtgggagatt   600
gatctgagag tggctcaaac gttgctgcct acgaacgttc cgattggaga agtctcttgt   660
ccaatgcagt cggtagtgaa actgctggat gatcagctgc cagatgacag cctgatacgg   720
aggtatccca aggaagccgc cgtcgctttg gctaaacgaa acggggaat acaatggatg   780
gacgtatcag aaggcaccgt gatgaacgag gctgtcaacg ctgttgcagc tagtgcactg   840
gcaccttcag catcagcccc accottagaa gagaagtcaa agttaaccga acaagcgatg   900
gatctcgtga ccgcggctga gcctgagata attgcctcac tcgcgccagt tcccgcaccc   960
gtgtttgcca taccacctaa accagcagat tataatgtgc gtactctgag gatcgacgag   1020
gccacttggc tgcgaatgat tccaaaatca atgaacacac cttttcaaat ccaggtgact   1080
gataacacag gaactaattg gcatctcaat ttgaggggg ggactcgtgt agtgaatctg   1140
gaccaaatcg ctccgatgcg gtttgtatta gatctagggg gaaagagtta taaagagacg   1200
agctgggatc caaacggcaa gaaggtcgga ttcatcgttt ttcaatcgaa gataccattc   1260
gaactttgga ctgctgcttc acagatcggt caagccacga tggttaacta tgtccaacta   1320
tacgctgaag acagctcatt taccgcgcag tctatcattg ctactacctc tttggcttat   1380
aactatgagc ctgagcagtt gaataagact gaccctgaga tgaattatta tcttttggcg   1440
acctttatag actcagccgc tataacgcca acgaatatga cacagcctga tgtttgggat   1500
gccttgctga cgatgtcccc actatcagct ggcgaggtga cagtgaaggg tgcggtagtg   1560
agtgaagtag tccctgcaga cttgataggg agctacactc cagaatccct aaacgcctca   1620
cttccgaatg atgctgctag atgcatgatc gatagagctt cgaagatagc cgaagcaatc   1680
aagattgatg atgatgctgg accagatgaa tattccccaa actctgtacc aattcaaggt   1740
cagcttgcta tctcgcaact cgaaactgga tatggtgtgc gaatattcaa ccctaaaggg   1800
atcctttcta aaattgcatc tagggcaatg caggcttttca ttggtgaccc gagcacaatc   1860
atcacgcagg cggcgccagt gttatcgac aagaataatt ggattgcatt ggcacaggga   1920
gtgaaaacta gtctgcgtac taaaagtcta tcagcgggag tgaagactgc agtgagtaag   1980
ctgagctcat ctgagtctat ccagaattgg actcaaggat tcttggataa agtgtcagcg   2040
catttttccag caccaaagcc cgattgtccg actacggag atagtggtga atcgtctaat   2100
cgccgagtga agcgcgactc atacgcagga gtggtcaaac gtgggtacac acgttaggcc   2160
gctcgccctg gtgacgcggg gttaagggat gcaggcaaat catc                    2204
```

SEQ ID NO: 7　　　　　　moltype = DNA　length = 2241
FEATURE　　　　　　　　　Location/Qualifiers
source　　　　　　　　　1..2241
　　　　　　　　　　　　mol_type = genomic DNA
　　　　　　　　　　　　organism = Reovirus
SEQUENCE: 7

```
gctaaagtga ccgtggtcat ggcttcattc aagggattct ccgccaacac tgttccagtt   60
tctaaggcca agcgtgacat atcatctctt gccgctactc ctggacttcg ttcacaatcc   120
ttcactccgt ctgtggatat gtctcaatcg cgtgaattcc tcacaaaggc aattgagcaa   180
gggtccatgt ctatacctta tcagcatgtg aatgtaccga aagttgatcg taaagttgtt   240
agcctggtag tgcgaccttt ctcttcaggt gctttctcta tctctggagt gatttcgcca   300
gcccatgcct atctactaga gtgtctaccc cagcttgagc aggcgatggc ttttgttgct   360
tcacctgagt cttttccaggc ttccgacgtc gcgaagcgct ttgccataaa gccaggtatg   420
agcctccagg atgccatcac tgcctttatt aactttgtgt ccgcgatgct gaaaatgacg   480
gtgactcgtc aaaacttga cgttattgtg gctgagatcg agaggcttgc ttcaaccagc   540
gtgtccgtca ggactgaaga agcgaaggtt gctgatgagg agctaatgct attcgggtta   600
gatcatagag ggcacagca gctgatgtt tctgacgcta aagggataat gaaggctgct   660
gatattcaga caactcatga tgtccatttg gcaccaggcg ttggtaatat tgatcctgaa   720
atctataacg agggggcggtt catgttcatg cagcacaagc cacttgcggc ggatcaatcg   780
tatttcacct tggagactgc ggattatttc aagatttatc caacatacga tgaacatgat   840
```

-continued

```
ggcaggatgg ctgaccaaaa gcagtcggga ttgatactgt gtactaagga cgaggtattg    900
gctgagcaaa ctatatttaa actggacgcc cctgatgaca agactgttca tctgttggat    960
cgcgatgacg accacgttgt tgccagattt actaaggtat ttatagagga cgtggctccc   1020
gggcatcatg ctgctcaaag atcgggacaa cgctctgtgc ttgatgacct atatgcgaat   1080
acgcaagtga tttccattac ttctgctgct ttaaagtggt tggtcaagca cggcgtatct   1140
gatggaatcg tgaacaggaa gaatgtcaaa gtgtgtgttg gttttgaccc cctgtacacc   1200
ttgtctacac ataacggggt gtccttatgt gccctgctga tggacgaaaa actctctgtg   1260
ctgaacagtg cgtgtcgtat gacgttacgc tcactcatga agaccggacg cgacgttgat   1320
gcacacagag cttttcagcg agtcctctct caaggataca catcgctaat gtgctactat   1380
catccttcac ggaagttggc atatggtgag gtgctctttc tagaacgatc caatgacgtg   1440
acagatggga tcaagcttca gttggacgca tctagacagt gtcatgaatg tcctgtgttg   1500
cagcagaaag tggttgagtt agagaaacag attattatgc agaagtcaat ccagtcagac   1560
cctaccccag tggcgctgca accattgttg tctcagttgc gtgagttgtc tagtgaagtt   1620
actaggctac agatggagtt gagtcgagct cagtccctga atgctcagtt ggaggcggat   1680
gtcaagtcag ctcaatcatg tagcttggat atgtatctga gacaccacac ttgcattaat   1740
ggtcatgcta aagaagatga attgcttgac gctgtgcgtg tcgcgccgga tgtgaggaga   1800
gaaatcatgg aaaagaggag tgaagtgaga caaggttggt gcgaacgtat ttctaaggaa   1860
gcagctgcca aatgtcaaac tgttattgat gacctgactt tgatgaatgg aaagcaagca   1920
caagagataa cagaattacg tgattcggct gaaaaatatg agaaacagat tgcagagctg   1980
gtgagtacca tcacccaaaa ccagataacg tatcagcaag agctacaagc cttggtagcg   2040
aaaaatgtgg aattggacgc gttgaatcag cgtcaggcta agtctttgcg tattactccc   2100
tctcttctat cagccactcc tatcgattca gttgatgatg ttgctgactt aattgatttc   2160
tctgttccaa ctgatgagtt gtaaataatc cgtgatgcag tgttgcccta atcccttaag   2220
ccttccgac ccccattcat c                                               2241
```

```
SEQ ID NO: 8             moltype = DNA   length = 3854
FEATURE                 Location/Qualifiers
source                  1..3854
                        mol_type = genomic DNA
                        organism = Reovirus
SEQUENCE: 8
gctacacgtt ccacgacaat gtcatccatg atactgactc agtttggacc gttcattgag     60
agcatttcag gtatcactga tcaatcgaat gacgtgtttg aagatgcagc aaaagcattc    120
tctatgttta ctcgcagcga tgtctacaag gcgctggatg aaataccttt ctctgatgat    180
gcgatgcttc caatccctcc aactatatat acgaaaccat ctcacgattc atattattac    240
attgatgctc taaaccgtgt gcgtcgcaaa acatatcagg gccctgatga cgtgtacgta    300
cctaattgtt ctattgttga attgctggag ccacatgaga ctctgacatc ttatgggcgg    360
ttgtccgagg ccatcgagaa tcgtgccaag gatggggaca gccaagccag aatcgccaca    420
acgtatggta gaatcgctga atctcaagct cgacagatta aggctccatt ggagaagttt    480
gtgttggcac tattagtggc cgaagcaggg gggtctttat atgatccagt tttgcagaag    540
tatgatgaga ttccagatct atcgcataat tgcccttat ggtgttttag agagatctgt    600
cgtcacatat ctggtccatt accagatcgg gcaccttatc tttacttatc tgcagggggt    660
ttctggttaa tgtcaccacg aatgacgtct gcaatccctc cgctactatc cgatcttgtt    720
aatttagcta ttttgcaaca aactgcgggt ttagatccat cattagtgaa attgggagta    780
cagatatgcc ttcatgcagc agctagctca agttatgcat ggtttatctt aaagactaag    840
tctatttttg ctcaaaacac gttgcacagt atgtatgaat ctctagaagg gggatactgt    900
cctaatcttg aatggttaga gcctagatca gactataagt tcatgtacat ggggagtcatg    960
ccattgtccg ctaagtatgc taggtcggcg ccgtccaatg ataagaaagc gcgggaactt   1020
ggcgagaaat atggactgag ctcagtcgtc ggtgagcttc gtaaacggac aaaagacgtat   1080
gttaaacatg actttgcttc agtgaggtac attcgtgacg ctatggcatg tactagcggt   1140
attttcttgg taagaacacc caccgaaacg gtattgcaag aatatacgca gagtccggag   1200
attaaggttc ccattcccca gaaagactgg acaggcccaa taggtgaaat cagaattcta   1260
aaaagatacaa caagttccat cgcgcgttac ttatatagaa catggtactt ggcagcggcg   1320
agaatggcgc ctcaaccacg tacgtgggat ccattgtttc aagcgattat gagatctcaa   1380
tacgtgacag ctaggggtgg atctggcgca gcactccgcg aatctttgta tgcaatcaat   1440
gtgtcgttac ctgatttcaa gggcttacca gtgaaggcag caactaagat attccaggcg   1500
gcacaattag cgaacttgcc gttctcccac acatcagtgg ctatactagc tgacacttca   1560
atgggattgc gaaatcaggt gcagaggcgg ccacgatcca ttatgccatt aaatgtgccc   1620
cagcagcagg tttcggcgcc ccatacattg acagcggatt acattaacta ccacatgaat   1680
ctatcaacca cgtctggtag tgcggtcatt gagaaggtga ttcctttagg tgtatacgct   1740
tcgagccctc ctaaccagtc gatcaacatt gacatatctg cgtgtgacgc tagtattact   1800
tgggattct ttctgtcagt gattatggcg gctatacacg aaggtgtcgc tagtagctcc   1860
attggaaaac catttatggg ggttcctgca tccattgtaa atgatgagtc tgtcgttgga   1920
gtgagagctg ctaggccgat atcgggaatg cagaacatga ttcagcatct atcgaaacta   1980
tataaacgtg gattttcata tagagtaaac gattcttttt ctccaggtaa cgattttact   2040
catatgacta ccactttccc gtcaggttca acagccacct ctactgagca tactgctaat   2100
aatagtacga tgatggaaac tttcctgaca gtatggggac ccgaacatac tgacgaccct   2160
gacgtcttac gtttaatgaa gtctttaact attcaaagga attacgtatg tcaaggtgat   2220
gatggattaa tgattatcga tgggactact gctggtaagg tgaacagtga aactattcag   2280
aagatgctag aattaatctc aaaatatggt gaggaattcg gatggaaata tgacatagcg   2340
tacgatggga ctgccgaata cttaaagcta tacttcatat ttggctgtcg aattccaaat   2400
cttagtcgcc atccaatcgt ggggaaagaa cgggcgaatt cttcagcaga ggagccatgg   2460
ccagcaattc tagatcagat tatgggtgtc ttctttaatg gtgttcatga tgggttacag   2520
tggcagcggt ggatacgtta ttcatgggct ctatgctgtc ctttctcacg tcaaagaaca   2580
atgattggtg agagcgtggg ttaccttcaa tatcctatgt ggtcttttgt ctactgggga   2640
ttaccactgg ttaaagcgtt tgggtcagac ccatggatat tttcttggta catgcctact   2700
ggagatctgg gaatgtatag ttggattagc ttgatacgcc ctctgatgac aagatggatg   2760
gtggctaatg gttacgtaac tgacagatgc tcacccgtat cgggaacgc agattatcgc   2820
aggtgtttca atgaacttaa actatatcaa ggttattata tggcacaatt gcccaggaat   2880
```

-continued

```
cctaagaagt ctggacgagc ggcccctcgg gaggtaagag aacaattcac tcaggcatta   2940
tccgactatc tactgcaaaa tccagagctg aagtcacgtg tgctacgtgg tcgtagtgag   3000
tgggagaaat atggagcggg gataattcac aatcctccgt cattattcga tgtgccccat   3060
aaatggtatc agggtgcgca agaggcagca atcgctacga gagaagagct ggcagaaatg   3120
gatgagacat taatgcgcgc tcgaaggcac agatattcga gcttttcaaa gttattagag   3180
gcgtatctgc tcgtgaaatg gcgaatgtgc gaggcccgcg aaccgtcggt ggatttgcga   3240
ttaccattat gtgcgggtat tgacccatta aactcagatc cttttctcaa gatggtaagc   3300
gttggaccaa tgctccagag tacgagaaag tactttgctc agacactatt catggcaaag   3360
acggtgtcgg gtcttgacgt taacgcgatt gatagcgcgt tattacgact gcgaacatta   3420
ggtgctgata agaaagcatt aacggcgcag ttattaatgg tggggcttca ggagtcagaa   3480
gcggacgcat tggccgggaa gataatgcta caggatgtga atactgtgca attagccaga   3540
gtggttaact tagctgtgcc agatacttgg atgtcgttag actttgactc tatgttcaaa   3600
caccacgtca agctgcttcc caaagatgga cgtcatctaa atactgatat tcctcctcga   3660
atgggatggt tacgggccat tttacgattc ttaggtgccg gaatggtaat gactgcgact   3720
ggagttgctg tcgacatcta tctgtgaggat atacatgcg gtggtcggtc acttggacag   3780
agattcatga cttggatgcg acaggaagga cggtcagcgt gagtctacca tgggtcgtgg   3840
tgcgtcaact catc                                                     3854
```

```
SEQ ID NO: 9         moltype = DNA   length = 3916
FEATURE              Location/Qualifiers
source               1..3916
                     mol_type = genomic DNA
                     organism = Reovirus
SEQUENCE: 9
gctaaatggc gcgatggcga acgtttgggg ggtgagactt gcagactcgt tatcttcacc   60
cactattgag acacgaacgc gtcagtatac cttacacgat ctttgctcag acctagatgc   120
taatccgggg aggggaaccgt ggaaacctct gcgtaatcag cgtactaata atattgtggc   180
tgtgcaatta ttcagaccat tgcagggtt agttttagat acccagcttt atggatttcc   240
aggagcattt gatgactggg agcgattcat gagagagaag ctgcgtgtgc taaagtatga   300
agtattgcgc atctatccaa tcagcaacta tagcaatgaa catgtcaacg tcttcgtagc   360
caatgctttg gtgggcgctt tcctgtcgaa tcaagctttc tatgacctgc taccgttgtt   420
gataattaat gacactatga ttggtgatct acttggcacg ggggcatcgc tatcacagtt   480
ctttcaatct catggagatg tgctggaagt cgcagctggt cgtaagtatc tgcagatgga   540
aaactactcc aacgatgacg atgatcctcc attatttgcg aaagacctgt cagattatgc   600
taaagcattc tacagtgaca catatgaagt gttggacagg ttcttttgga cgcatgactc   660
ttcagcgggg gtcttagtgc attatgataa gccaacgaat ggtcatcact atctgctggg   720
tactttgact cagatggtca gtgcacctcc ttatattatt aacgctactg acgcaatgtt   780
gcttgaatcc tgtctagaac agttctcagc taatgtgcgt gcgagacctg cgcaacccgt   840
tacacgctta gaccaatgct atcatttaag atgggagaca caatatgtag gagaagattc   900
actgacatat cggttggggg tgttatcctt gctggctacc aatggatatc aattagctag   960
accgattcca agacagttga cgaatcgatg gttgtcgagc tttgtgagtc aaattatgtc   1020
tgacggcgtc aacgagactc cactgtggcc ccaagaaagg tatgtgcaga tcgcttatga   1080
ttcaccatcc gttgttgatg gggctacgca atatggctat gtcaggaaga atcaactcag   1140
actcggcatg agaatatcgg cgctgcaatc gctgagtgat acgccctcgc cggtacagtg   1200
gcttccacaa tacaccatcg accaggcagc gatggacgaa ggcgatctga tggttagtcg   1260
gcttacgcaa ctcccgttac gtcctgatta tggtaatatc tgggtcggcg atgcgctatc   1320
ctattatgtg gactacaatc ggagtcatcg agtcgtgctt tcatcggaac ttcctcagct   1380
tccggacaca tattttgatg gcgatgaaca gtatgggcgc agcctgttct cactagctcg   1440
taagattggt gaccgctcgt tagtgaaaga tacggctgtc ttgaagcacg cttaccaagc   1500
catcgatcca aatactggta aggagtatct gagatctcgg caatctgtcg catattttgg   1560
tgcatcagcg ggtcattctg gtgccgacca gccgttagtc atagagccct ggattcaagg   1620
gaaaatcagt ggtgtgccgc caccctcctc agtcgcgacag ttcggctatg atgttgcccg   1680
tggcgcgatc gtcgatctgg cgagaccatt tccttctgga gattatcaat ttgtctattc   1740
ggatgttgac caggtggtcg atggccatga cgatctgagt atatcatctg gactggtgga   1800
gagcctttg tcttcatgca tgcacgccac agcaccggg ggctcatttg ttgttaagat   1860
aaattttccg actagacccg tatggcacta catcgaacag aagatcttgc ccaatattac   1920
gtcatacatg ttgatcaagc ctttcgtcac caacaacgtc gaattgttct tcgtcgcttt   1980
cggtgtgcat caacactcat cacttacttg gacatctgga gtgtacttct tcttggtgga   2040
ccattttat cgttatgaga ctttatctac gatctcacga caattgcgt cttttgggta   2100
tgttgatgat gggtcttccg tgactggtat cgagacaatt agtattgaga acctggctt   2160
ctcgaatatg acccaggccg ctcgcattgg tatctcagga ttgtgtgcta atgtaggtaa   2220
cgcgcgtaag tccattgcca tttacgaatc tcatggggcc agagtattaa ctatcacatc   2280
aaggagatct ccggcatcag ctagaagaaa gtctaggttg cgatatttgc cattaatagaa  2340
ccctaggtcg ttagaggtac aggcgcgcac tattctggca gctgatccag tgttatttga   2400
aaacgtgagc ggagcgtcac cccatgtttg tctgacaatg atgtacaact tcgaagtgtc   2460
gtcagcggta tatgatggag acgttgtgct agatcttggg acgggaccag aggctaaaat   2520
ccttgaactg atacccgcaa cctctccagt cacatgcgtg gacatacggc ctacagcgca   2580
gcctagtgga tgttggaacg ttcgtaccac gttccttgag ttagattatt tgagcgatgg   2640
atggatcact ggggtgcgtg gggacatagt tacttgtatg ttatcttttg gggccgctgc   2700
cgctggaaaa tcaatgactt ttgacgctgc gtttcagcaa ttaatcaaag tattatccaa   2760
gagtacggct aatgttgtgc tggtgcaggt taactgccct acagacgtgg tgaggagcat   2820
taagggctac ctagagatag attcgactaa caagaggtat aggttcccca aatttggtcg   2880
agacgagccg tactctgaca tggatgcgct ggagaaaata tgtcgtaccg cctggccaaa   2940
ctgctcaatt acctgggttc cattgtcata cgacttgccg tggactagac tggcattatt   3000
agagtccacg acattgagta gcgcgtcgat tagaattgct gagctgatgt ataaatacat   3060
gcctattatg aggattgata ttcatggact acccatggaa aagcgaggta acttcatagt   3120
ggggcagaac tgctcattag taatccctgg tttttaatgcg caggatgtct ttaactgtta   3180
tttcaattcc gccctcgctt ctcgactga agatgtcaat gctgcgatga ttccccaagt   3240
gtctgcgcag tttgatgcga ctaagggtga gtggacgttg gatatggtct tctccgacgc   3300
```

-continued

```
aggaatctat accatgcagg ctctagtggg atctaatgct aatccagtct ctttgggttc   3360
ctttgtagtt gattctccag atgtagatat aactgacgct tggccagctc agttagactt   3420
tacgatcgcg ggaactgatg tcgatataac agttaatcct tattaccgtc tgatgacctt   3480
tgtaaggatc gatggacagt ggcagattgc caatccagac aaatttcaat tcttttcgtc   3540
ggcgtctggg acgttagtga tgaacgtcaa attagatatc gcagataaat atctactata   3600
ctatatacga gatgtccagt ctcgagatgt tggcttttac attcagcatc cacttcaact   3660
tttgaatacg atcacattgc caaccaacga ggaccttttt ctgagcgcac ctgacatgcg   3720
agagtgggca gttaaggaaa gcggtaacac gatatgtata ctcaatagtc aagggtttgt   3780
gctacctcaa gattgggatg tgttaacaga taccataagt tggtccccat cgatacccac   3840
atacattgtg ccaccgggtg attatacctt gactcctctg taactcactg tccctcgtga   3900
gcgcgcctaa ttcatc                                                   3916

SEQ ID NO: 10            moltype = DNA   length = 3901
FEATURE                  Location/Qualifiers
source                   1..3901
                         mol_type = genomic DNA
                         organism = Reovirus
SEQUENCE: 10
gctaatcgtc aggatgaagc ggattccaag gaagacaaag ggcaaatcca gcggaaaggg   60
caatgactca acagagagag cggacgatgg ctcgagccaa ttaagagaca agcaaaacaa   120
taaggctggc cccgccacta cggagcctgg cacatccaac cgagagcaat acaaagctcg   180
accaggtatt gcatctgtgc agagggccac tgaaagtgcca cgaagaataa   240
tgacgaaggg acgccagata agaaaggaaa tactaagggc gacctagtta atgagcatag   300
tgaggctaaa gacgaggcgg atgaagcgac gaagaagcag gcaaaggata cagacaaaag   360
taaagcgcaa gtcacatatt cagacactgg tatcaataat gctaatgaac tgtcaagatc   420
tgggaatgtg gataatgagg gtggaagtaa tcagaagccg atgtctacca gaatagctga   480
ggcaacgtct gctatagtgt cgaaacatcc tgcgcgtgtt gggctgccac ctaccgctag   540
cagtggtcat gggtatcagt gccatgtctg ttctgcagtc ctgtttagtc ctttagacct   600
agatgcccac gtcgcctcac atggtttgca tggtaacatg acattaacat cgagtgatat   660
ccagcgacat ataactgagt tcatcagctc atggcaaaat catcctattg ttcaagtttc   720
ggctgatgtc gaaaataaga aaactgctca attgcttcac gctgacactc ctcgactcgt   780
cacttgggat gctggtttgt gtacttcatt caaaatcgtc ccgattgtgc cagctcaggt   840
gccgcaggat gtactggcct atacgttttt cacctcttca tacgctatcc aatcaccgtt   900
tccagaggcg gcagtgtcta ggattgtggt gcatacgaga tgggcatcta atgttgactt   960
tgaccgagac tcgtctgtca tcatggcgcc acctacagaa aacaatatcc atttgtttaa   1020
acagttacta aatactgaaa ccctgtctgt aaggggggct aatccgctaa tgttcagggc   1080
gaatgtgttg catatgttgc tagagttcgt attagataac ttgtatctga acagacatac   1140
gggattctct caagaccaca cgccatttac tgaggggtgct aatttgcgtt cacttcctgg   1200
ccccgatgct gagaaatggt actcgattat gtatccaacg cgcatgggaa cgccgaatgt   1260
atccaaaata tgtaatttcg tcgcctcttg tgtgcgaaat cgggttggac ggtttgatcg   1320
agcacagatg atgaacggag ctatgtcaga gtgggtggat gtcttcgaga cttcagacgc   1380
gctaaccgtc tccattcgag gtcgatggat ggctagacta gctcgcatga acataaatcc   1440
aacagagatc gaatgggcat tgactgaatg tgcacaagga tatgtgactg tcacaagtcc   1500
ttacgctcct agcgtaaata gattgatgcc ctatcgtatc tccaacgctg agcggcaaat   1560
atcacagata atcaggatca tgaacattgg caataacgcg acggtgatac aacctgttct   1620
gcaagatatt tcggtactcc ttcaacgcat atcaccactc caaatagatc caactattat   1680
ttccaacact atgtcaacag tctcggagtc tactactcag accctcagcc gccgtcctc   1740
aattttgggt aaactacgac caagcaactc agattttctt agttttagag tcgcgttggc   1800
tggatggctt tataatgggg ttgtgacgac ggtgattgat gatagttcat atccaaaaga   1860
cggcggcagc gtgacctcac ttgaaaatct gtgggatttc ttcatccttg cgcttgctct   1920
accactgaca actgaccccct gtgcacctgt gaaagcattc atgaccctag ccaacatgat   1980
ggttggtttc gagacaatcc ctatggataa tcagatctat actcaatcga gacgcgcgag   2040
tgctttctca acgcctcaca cgtggccacg atgctttatg aacatccagt taatttctcc   2100
aatcgacgct cccatcttgc gacagtgggc tgaaattatt catagatact ggcctaaccc   2160
ttcacagatt cgttatggtg caccgaacgt tttcggctcg gcaaatttgt tcactccacc   2220
tgaggtgctg ttattgccaa tcgatcatca accagctaat gtaacaacgc caacgctgga   2280
cttcaccaat gagttaacta attggcgcgc tcgtgtctgt gagcttatga agaatctcgt   2340
tgataaccaa agatatcaac ctggatggac acaaagtcta gtctcgtcaa tgcgcggaac   2400
gctagacaaa ttgaagttga ttaaatcgat gacaccaatg tatctgcaac agctggctcc   2460
ggtagagtta gcagtgatag ctcccatgtt gcctttttcca cctttccagg tgccatacgt   2520
ccgtctcgat cgtgacagag ttccaacaat ggttggagta acacgacatt cacgagatac   2580
tattactcag ccggcgctat cgctgtcgac aaccaatact actgttggcg tgccactagc   2640
tctagacgcg agggctatca ccgttgcgct gttgtcaggg aaatatccgc cggatttggt   2700
gacaaatgta tggtacgctg atgccattta cccaatgtat gcagacacgg aggtgttctc   2760
taatcttcag agagacatga ttacctgcga ggccgtgcag acattagtga ctctggtggc   2820
gcaaatatca gagacccagt atcctgtaga taggtatctt gattggatcc catcactgag   2880
agcatcggcg gcgacggcgg cgacatttgc tgagtgggtt aatacttcaa tgaagacggc   2940
gtttgatttg tctgatatgc tgttagagcc tctcctaagc ggtgatccga ggatgactca   3000
actagcgatt cagtatgcag agtacaatgg cagaacgttt aatatcatac ctgaaatgcc   3060
aggttcagta attgctgact gcgttcaatt aacagcagaa gtctttaatc acgaatataa   3120
cctgtttggg attgcgcggg gtgatatcat cattggccgt gttcagtcga cacatttgtg   3180
gtcaccgctg gctcctccac ctgacctggt gtttgatcgt gataccccctg gtgttcacat   3240
cttcggacga gattgccgta tatcgtttgg aatgaatggc gccgcgccaa tgattagaga   3300
tgagactgga ctgatggtgc cttttgaagg aaattggatt ttcccactgg cgctttggca   3360
aatgaataca cgatatttta atcaacagtt cgacgcgtgg attaagacag gagagttgcg   3420
aatccgcatt gagatggggcg cgtatccata tatgttgcat tactatgatc cacgtcagta   3480
cgctaatgca tggaatttaa catccgcctg gcttgaagaa attacgccga cgagcatccc   3540
atccgtgcct ttcatggtgc ccatttcaag tgatcatgac atttcctctg ccccagctgt   3600
ccaatatatc atttcaactg aatataatga tcggtctctg ttctgcacta actcatcatc   3660
```

```
tccccaaacc atcgctggac cagacaaaca cattccagtt gagagatata acattctgac   3720
caacccgac  gctccaccca cgcagataca actgcctgaa gtcgttgact tgtacaacgt   3780
cgtcacacgc tatgcgtatg agactccgcc tattaccgct gttgttatgg gtgttccttg   3840
atcctcatcc tcccaacagg tgctagagca ttgcgctcaa tgctagttgg gccgattcat   3900
c                                                                   3901
```

SEQ ID NO: 11                   moltype = AA   length = 455
FEATURE                         Location/Qualifiers
source                          1..455
                                mol_type = protein
                                organism = Reovirus
SEQUENCE: 11
```
MDPRLREEVV RLIIALTSDN GASLSKGLES RVSALEKTSQ IHSDTILRIT QGLDDANKRI   60
IALEQSRDDL VASVSDAQLA ISRLESSIGA LQTVVNGLDS SVTQLGARVG QLETGLAELR   120
VDHDNLVARV DTAERNIGSL TTELSTLTLR VTSIQADFES RISTLERTAV TSAGAPLSIR   180
NNRMTMGLND GLTLSGNNLA IRLPGNTGLN IQNGGLQFRF NTDQFQIVNN NLTLKTTVFD   240
SINSRIGATE QSYVASAVTP LRLNSSTKVL DMLIDSSTLE INSSGQLTVR STSPNLRYPI   300
ADVSGGIGMS PNYRFRQSMW IGIVSYSGSG LNWRVQVNSD IFIVDDYIHI CLPAFDGFSI   360
ADGGDLSLNF VTGLLPPLLT GDTEPAFHND VVTYGAQTVA IGLSSGGAPQ YMSKNLWVEQ   420
WQDGVLRLRV EGGGSITHSN SKWPAMTVSY PRSFT                             455
```

SEQ ID NO: 12                   moltype = AA   length = 418
FEATURE                         Location/Qualifiers
source                          1..418
                                mol_type = protein
                                organism = Reovirus
SEQUENCE: 12
```
MARAAFLFKT VGFGGLQNVP INDELSSHLL RAGNSPWQLT QFLDWISLGR GLATSALVPT   60
AGSRYYQMSC LLSGTLQIPF RPNHRWGDIR FLRLVWSAPT LDGLVVAPPQ VLAQPALQAQ   120
ADRVYDCDDY PFLARDPRFK HRVYQQLSAV TLLNLTGFGP ISYVRVDEDM WSGDVNQLLM   180
NYFGHTFAEI AYTLCQASAN RPWEYDGTYA RMTQIVLSLF WLSYVGVIHQ QNTYRTFYFQ   240
CNRRGDAAEV WILSCSLNHS AQIRPGNRSL FVMPTSPDWN MDVNLILSST LTGCLCSGSQ   300
LPLIDNNSVP AVSRNIHGWT GRAGNQLHGF QVRRMVTEFC DRLRRDGVMT QAQQNQVEAL   360
ADQTQQFKRD KLETWAREDD QYNQAHPNST MFRTKPFTNA QWGRGNTGAT SAAIAALI    418
```

SEQ ID NO: 13                   moltype = AA   length = 254
FEATURE                         Location/Qualifiers
source                          1..254
                                mol_type = protein
                                organism = Reovirus
SEQUENCE: 13
```
MASSLRAAIS KIKRDDVGQQ VCPNYVMLRS SVTTKVVRNV VEYQIRTGGF FSCLAMLRPL   60
QYAKRERLLG QRNLERISTR DILQTRDLHS LCMPTPDAPM SNHQASTMRE LICSYFKVDH   120
ADGLKYIPMD ERYSPSSLAR LFTMGMAGLH ITTEPSYKRV PIMHLAADLD CMTLALPYMI   180
TLDGDTVVPV APTLSAEQLL DDGLKGLACM DMDVRWTRIA GRLVIRVWTL HAASTSCIAR   240
RQQKPSVCLR HALC                                                    254
```

SEQ ID NO: 14                   moltype = AA   length = 366
FEATURE                         Location/Qualifiers
source                          1..366
                                mol_type = protein
                                organism = Reovirus
SEQUENCE: 14
```
MASSLRAAIS KIKRDDVGQQ VCPNYVMLRS SVTTKVVRNV VEYQIRTGGF FSCLAMLRPL   60
QYAKRERLLG QRNLERISTR DILQTRDLHS LCMPTPDAPM SNHQASTMRE LICSYFKVDH   120
ADGLKYIPMD ERYSPSSLAR LFTMGMAGLH ITTEPSYKRV PIMHLAADLD CMTLALPYMI   180
TLDGDTVVPV APTLSAEQLL DDGLKGLACM DISYGCEVDA NSRPAGDQSM DSSRCINELY   240
CEETAEAICV LKTCLVLNCM QFKLEMDDLA HNAAELDKIQ MMIPFSERVF RMASSFATID   300
AQCFRFCVMM KDKNLKIDMR ETTRLWTRSA SDDSVATSSL SISLDRGRWV AADASDARLL   360
VFPIRV                                                             366
```

SEQ ID NO: 15                   moltype = AA   length = 365
FEATURE                         Location/Qualifiers
source                          1..365
                                mol_type = protein
                                organism = Reovirus
SEQUENCE: 15
```
MEVCLPNGHQ VVDLINNAFE GRVSIYSAQE GWDKTISAQP DMMVCGGAVV CMHCLGVVGS   60
LQRKLKHLPH HRCNQQIRHQ DYVDVQFADR VTAHWKRGML SFVAQMHEMM NDVSPDDLDR   120
VRTEGGSLVE LNRLQVDPNS MFRSIHSSWT DPLQVVDDLD TKLDQYWTAL NLMIDSSDLI   180
PNFMMRDPSH AFNGVKLKGD ARQTQFSRTF DSRSSLEWGV MVYDYSELDH DPSKGRAYRK   240
ELVTPARDFG HFGLSHYSRA TTPILGKMPA VFSGMLTGNC KMYPFIKGTA KLKTVRKLVE   300
AVNHAWGVEK IRYALGPGGM TGWYNRTMQQ APIVLTPAAL TMFPDTIKFG DLNYPVMIGD   360
PMILG                                                             365
```

SEQ ID NO: 16                   moltype = AA   length = 736
FEATURE                         Location/Qualifiers
source                          1..736
                                mol_type = protein

```
                        organism = Reovirus
SEQUENCE: 16
MAYIAVPAVV DSRSSEAIGL LESFGVDAGA DANDVSYQDH DYVLDQLQYM LDGYEAGDVI    60
DALVHKNWLH HSVYCLLPPK SQLLEYWKSN PSAIPDNVDR RLRKRLMLKK DLRKDDEYNQ   120
LARAFKISDV YAPLISSTTS PMTMIQNLNR GEIVYTTTDR VIGARILLYA PRKYYASTLS   180
FTMTKCIIPF GKEVGRVPHS RFNVGTFPSI ATPKCFVMSG VDIESIPNEF IKLFYQRVKS   240
VHANILNDIS PQIVSDMINR KRLRVHTPSD RRAAQLMHLP YHVKRGASHV DVYKVDVVDM   300
LFEVVDVADG LRNVSRKLTM HTVPVCILEM LGIEIADYCI RQEDGMLTDW FLLLTMLSDG   360
LTDRRTHCQY LINPSSVPPD VILNISITGF INRHTIDVMP DIYDFVKPIG AVLPKGSFKS   420
TIMRVLDSIS ILGIQIMPRA HVVDSDEVGE QMEPTFEQAV MEIYKGIAGV DSLDDLIKWV   480
LNSDLIPHDD RLGQLFQAFL PLAKDLLAPM ARKFYDNSMS EGRLLTFSHA DSELLNANYF   540
GHLLRLKIPY ITEVNLMIRK NREGGELFQL VLSYLYKMYA TSAQPKWFGS LLRLLICPWL   600
HMEKLIGEAD PASTSAEIGW HIPREQLMQD GWCGCEDGFI PYVSIRAPRL VIEELMEKNW   660
GQYHAQVIVT DQLVVGEPRR VSAKAVIKGN HLPVKLVSRF ACFTLTAKYE MRLSCGHSTG   720
RGAAYSARLA FRSDLA                                                  736

SEQ ID NO: 17        moltype = AA  length = 708
FEATURE              Location/Qualifiers
source               1..708
                     mol_type = protein
                     organism = Reovirus
SEQUENCE: 17
MGNASSIVQT INVTGDGNVF KPSAETSSTA VPSLSLSPGM LNPGGVPWIA VGDETSVTSP    60
GALRRMTSKD IPDTAIINTD NSSGAVPSES ALVPYIDEPL VVVTEHAITN FTKAEMALEF   120
NREFLDKMRV LSVSPKYSDL LTYVDCYVGV SARQALNNFQ KQVPVITPTR QTMYVDSIQA   180
ALKALEKWEI DLRVAQTLLP TNVPIGEVSC PMQSVVKLLD DQLPDDSLIR RYPKEAAVAL   240
AKRNGGIQWM DVSEGTVMNE AVNAVAASAL APSASAPPLE EKSKLTEQAM DLVTAAEPEI   300
IASLAPVPAP VFAIPPKPAD YNVRTLRIDE ATWLRMIPKS MNTPFQIQVT DNTGTNWHLN   360
LRGGTRVVNL DQIAPMRFVL DLGGKSYKET SWDPNGKKVG FIVFQSKIPF ELWTAASQIG   420
QATVVNYVQL YAEDSSFTAQ SIIATTSLAY NYEPEQLNKT DPEMNYYLLA TFIDSAAITP   480
TNMTQPDVWD ALLTMSPLSA GEVTVKGAVV SEVVPADLIG SYTPESLNAS LPNDAARCMI   540
DRASKIAEAI KIDDDAGPDE YSPNSVPIQG QLAISQLETG YGVRIFNPKG ILSKIASRAM   600
QAFIGDPSTI ITQAAPVLSD KNNWIALAQG VKTSLRTKSL SAGVKTAVSK LSSSESIQNW   660
TQGFLDKVSA HFPAPKPDCP TSGDSGESSN RRVKRDSYAG VVKRGYTR                708

SEQ ID NO: 18        moltype = AA  length = 721
FEATURE              Location/Qualifiers
source               1..721
                     mol_type = protein
                     organism = Reovirus
SEQUENCE: 18
MASFKGFSAN TVPVSKAKRD ISSLAATPGL RSQSFTPSVD MSQSREFLTK AIEQGSMSIP    60
YQHVNVPKVD RKVVSLVVRP FSSGAFSISG VISPAHAYLL ECLPQLEQAM AFVASPESFQ   120
ASDVAKRFAI KPGMSLQDAI TAFINFVSAM LKMTVTRQNF DVIVAEIERL ASTSVSVRTE   180
EAKVADEELM LFGLDHRGPQ QLDVSDAKGI MKAADIQTTH DVHLAPGVGN IDPEIYNEGR   240
FMFMQHKPLA ADQSYFTLET ADYFKIYPTY DEHDGRMADQ KQSGLILCTK DEVLAEQTIF   300
KLDAPDDKTV HLLDRDDDHV VARFTKVFIE DVAPGHHAAQ RSGQRSVLDD LYANTQVISI   360
TSAALKWVVK HGVSDGIVNR KNVKVCVGFD PLYTLSTHNG VSLCALLMDE KLSVLNSACR   420
MTLRSLMKTG RDVDAHRAFQ RVLSQGYTSL MCYYHPSRKL AYGEVLFLER SNDVTDGIKL   480
QLDASRQCHE CPVLQQKVVE LEKQIIMQKS IQSDPTPVAL QPLLSQLREL SSEVTRLQME   540
LSRAQSLNAQ LEADVKSAQS CSLDMYLRHH TCINGHAEKD ELLDAVRVAP DVRREIMEKR   600
SEVRQGWCER ISKEAAAKCQ TVIDDLTLMN GKQAQEITEL RDSAEKYEKQ IAELVSTITQ   660
NQITYQQELQ ALVAKNVELD ALNQRQAKSL RITPSLLSAT PIDSVDDVAD LIDFSVPTDE   720
L                                                                 721

SEQ ID NO: 19        moltype = AA  length = 1267
FEATURE              Location/Qualifiers
source               1..1267
                     mol_type = protein
                     organism = Reovirus
SEQUENCE: 19
MSSMILTQFG PFIESISGIT DQSNDVFEDA AKAFSMFTRS DVYKALDEIP FSDDAMLPIP    60
PTIYTKPSHD SYYYIDALNR VRRKTYQGPD DVYVPNCSIV ELLEPHETLT SYGRLSEAIE   120
NRAKDGDSQA RIATTYGRIA ESQARQIKAP LEKFVLALLV AEAGGSLYDP VLQKYDEIPD   180
LSHNCPLWCF REICRHISGP LPDRAPYLYL SAGVFWLMSP RMTSAIPPLL SDLVNLAILQ   240
QTAGLDPSLV KLGVQICLHA AASSSYAWFI LKTKSIFPQN TLHSMYESLE GGYCPNLEWL   300
EPRSDYKFMY MGVMPLSAKY ARSAPSNDKK ARELGEKYGL SSVVGELRKR TKTYVKHDFA   360
SVRYIRDAMA CTSGIFLVRT PTETVLQEYT QSPEIKVPIP QKDWTGPIGE IRILKDTTSS   420
IARYLYRTWY LAAARMAAQP RTWDPLFQAI MRSQYVTARG GSGAALRESL YAINVSLPDF   480
KGLPVKAATK IFQAAQLANL PFSHTSVAIL ADTSMGLRNQ VQRRPRSIMP LNVPQQQVSA   540
PHTLTADYIN YHMNLSTTSG SAVIEKVIPL GVYASSPPNQ SINIDISACD ASITWDFFLS   600
VIMAAIHEGV ASSSIGKPFM GVPASIVNDE SVVGVRAARP ISGMQNMIQH LSKLYKRGFS   660
YRVNDSFSPG NDFTHMTTTF PSGSTATSTE HTANNSTMME TFLTVWGPEH TDDPDVLRLM   720
KSLTIQRNYV CQGDDGLMII DGTTAGKVNS ETIQKMLELI SKYGEEFGWK YDIAYDGTAE   780
YLKLYFIFGC RIPNLSRHPI VGKERANSSA EEPWPAILDQ IMGVFFNGVH DGLQWQRWIR   840
YSWALCCAFS RQRTMIGESV GYLQYPMWSF VYWGLPLVKA FGSDPWIFSW YMPTGDLGMY   900
SWISLIRPLM TRWMVANGYV TDRCSPVFGN ADYRRCFNEL KLYQGYYMAQ LPRNPKKSGR   960
AAPREVREQF TQALSDYLLQ NPELKSRVLR GRSEWEKYGA GIIHNPPSLF DVPHKWYQGA  1020
QEAAIATREE LAEMDETLMR ARRHRYSSFS KLLEAYLLVK WRMCEAREPS VDLRLPLCAG  1080
```

-continued

```
IDPLNSDPFL KMVSVGPMLQ STRKYFAQTL FMAKTVSGLD VNAIDSALLR LRTLGADKKA    1140
LTAQLLMVGL QESEADALAG KIMLQDVNTV QLARVVNLAV PDTWMSLDFD SMFKHHVKLL    1200
PKDGRHLNTD IPPRMGWLRA ILRFLGAGMV MTATGVAVDI YLEDIHGGGR SLGQRFMTWM    1260
RQEGRSA                                                             1267

SEQ ID NO: 20            moltype = AA  length = 1289
FEATURE                  Location/Qualifiers
source                   1..1289
                         mol_type = protein
                         organism = Reovirus
SEQUENCE: 20
MANVWGVRLA DSLSSPTIET RTRQYTLHDL CSDLDANPGR EPWKPLRNQR TNNIVAVQLF     60
RPLQGLVLDT QLYGFPGAFD DWERFMREKL RVLKYEVLRI YPISNYSNEH VNVFVANALV    120
GAFLSNQAFY DLLPLLIIND TMIGDLLGTG ASLSQFFQSH GDVLEVAAGR KYLQMENYSN    180
DDDDPPLFAK DLSDYAKAFY SDTYEVLDRF FWTHDSSAGV LVHYDKPTNG HHYLLGTLTQ    240
MVSAPPYIIN ATDAMLLESC LEQFSANVRA RPAQPVTRLD QCYHLRWGAQ YVGEDSLTYR    300
LGVLSLLATN GYQLARPIPR QLTNRWLSSF VSQIMSDGVN ETPLWPQERY VQIAYDSPSV    360
VDGATQYGYV RKNQLRLGMR ISALQSLSDT PSPVQWLPQY TIDQAAMDEG DLMVSRLTQL    420
PLRPDYGNIW VGDALSYYVD YNRSHRVVLS SELPQLPDTY FDGDEQYGRS LFSLARKIGD    480
RSLVKDTAVL KHAYQAIDPN TGKEYLRSRQ SVAYFGASAG HSGADQPLVI EPWIQGKISG    540
VPPPSSVRQF GYDVARGAIV DLARPFPSGD YQFVYSDVDQ VVDGHDDLSI SSGLVESLLS    600
SCMHATAPGG SFVVKINFPT RPVWHYIEQK ILPNITSYML IKPFVTNNVE LFFVAFGVHQ    660
HSSLTWTSGV YFFLVDHFYR YETLSTISRQ LPSFGYVDDG SSVTGIETIS IENPGFSNMT    720
QAARIGISGL CANVGNARKS IAIYESHGAR VLTITSRRSP ASARRKSRLR YLPLIDPRSL    780
EVQARTILPA DPVLFENVSG ASPHVCLTMM YNFEVSSAVY DGDVVLDLGT GPEAKILELI    840
PATSPVTCVD IRPTAQPSGC WNVRTTFLEL DYLSDGWITG VRGDIVTCML SLGAAAAGKS    900
MTFDAAFQQL IKVLSKSTAN VVLVQVNCPT DVVRSIKGYL EIDSTNKRYR FPKFGRDEPY    960
SDMDALEKIC RTAWPNCSIT WVPLSYDLRW TRLALLESTT LSSASIRIAE LMYKYMPIMR   1020
IDIHGLPMEK RGNFIVGQNC SLVIPGFNAQ DVFNCYFNSA LAFSTEDVNA AMIPQVSAQF   1080
DATKGEWTLD MVFSDAGIYT MQALVGSNAN PVSLGSFVVD SPDVDITDAW PAQLDFTIAG   1140
TDVDITVNPY YRLMTFVRID GQWQIANPDK FQFFSSASGT LVMNVKLDIA DKYLLYYIRD   1200
VQSRDVGFYI QHPLQLLNTI TLPTNEDLFL SAPDMREWAV KESGNTICIL NSQGFVLPQD   1260
WDVLTDTISW SPSIPTYIVP PGDYTLTPL                                     1289

SEQ ID NO: 21            moltype = AA  length = 1275
FEATURE                  Location/Qualifiers
source                   1..1275
                         mol_type = protein
                         organism = Reovirus
SEQUENCE: 21
MKRIPRKTKG KSSGKGNDST ERADDGSSQL RDKQNNKAGP ATTEPGTSNR EQYKARPGIA     60
SVQRATESAE MPMKNNDEGT PDKKGNTKGD LVNEHSEAKD EADEATKKQA KDTDKSKAQV    120
TYSDTGINNA NELSRSGNVD NEGGSNQKPM STRIAEATSA IVSKHPARVG LPPTASSGHG    180
YQCHVCSAVL FSPLDLDAHV ASHGLHGNMT LTSSDIQRHI TEFISSWQNH PIVQVSADVE    240
NKKTAQLLHA DTPRLVTWDA GLCTSFKIVP IVPAQVPQDV LAYTFFTSSY AIQSPFPEAA    300
VSRIVVHTRW ASNVDFDRDS SVIMAPPTEN NIHLFKQLLN TETLSVRGAN PLMFRANVLH    360
MLLEFVLDNL YLNRHTGFSQ DHTPFTEGAN LRSLPGPDAE KWYSIMYPTR MGTPNVSKIC    420
NFVASCVRNR VGRFDRAQMM NGAMSEWVDV FETSDALTVS IRGRWMARLA RMNINPTEIE    480
WALTECAQGY VTVTSPYAPS VNRLMPYRIS NAERQISQII RIMNIGNNAT VIQPVLQDIS    540
VLLQRISPLQ IDPTIISNTM STVSESTTQT LSPASSILGK LRPSNSDFSS FRVALAGWLY    600
NGVVTTVIDD SSYPKDGGSV TSLENLWDFF ILALALPLTT DPCAPVKAFM TLANMMVGFE    660
TIPMDNQIYT QSRRASAFST PHTWPRCFMN IQLLISPIDAP ILRQWAEIIH RYWPNPSQIR    720
YGAPNVFGSA NLFTPPEVLL LPIDHQPANV TTPTLDFTNE LTNWRARVCE LMKNLVDNQR    780
YQPGWTQSLV SSMRGTLDKL KLIKSMTPMY LQQLAPVELA VIAPMLPFPP FQVPYVRLDR    840
DRVPTMVGVT RHSRDTITQP ALSLSTTNTT VGVPLALDAR AITVALLSGK YPPDLVTNVW    900
YADAIYPMYA DTEVFSNLQR DMITCEAVQT LVTLVAQISE TQYPVDRYLD WIPSLRASAA    960
TAATFAEWVN TSMKTAFDLS DMLLEPLLSG DPRMTQLAIQ YQQYNGRTFN IIPEMPGSVI   1020
ADCVQLTAEV FNHEYNLFGI ARGDIIIGRV QSTHLWSPLA PPPDLVFDRD TPGVHIFGRD   1080
CRISFGMNGA APMIRDETGL MVPFEGNWIF PLALWQMNTR YFNQQFDAWI KTGELRIRIE   1140
MGAYPYMLHY YDPRQYANAW NLTSAWLEEI TPTSIPSVPF MVPISSDHDI SSAPAVQYII   1200
STEYNDRSLF CTNSSSPQTI AGPDKHIPVE RYNILTNPDA PPTQIQLPEV VDLYNVVTRY   1260
AYETPPITAV VMGVP                                                   1275

SEQ ID NO: 22            moltype = DNA  length = 3854
FEATURE                  Location/Qualifiers
source                   1..3854
                         mol_type = genomic DNA
                         organism = Reovirus
SEQUENCE: 22
gctacacgtt ccacgacaat gtcatccatg atactgactc agtttggacc gttcattgag     60
agcatttcag gtatcactga tcaatcgaat gacgtgtttg aagatgcagc aaaaagcattc    120
tctatgttta ctcgcagcga tgtctacaag gcgctggatg aaataccttt ctctgatgat    180
gcgatgcttc caatccctcc aactatatat acgaaaccat ctcacgattc atattattac     240
attgatgctc taaaccgtgt gcgtcgcaaa acatatcagg cgcctgatga cgtgtacgta     300
cctaattgtt ctattgttga attgctggag ccacatgaga ctctgacatc ttatgggcgg     360
ttgtccgagg ccatcgagaa tcgtgccaag gatgggggaca gccaagccag aatcgccaca     420
acgtatggta gaatcgctga atctcaagct cgacagatta aggctccatt ggagaagttt     480
gtgttggcac tattagtggc cgaagcaggg gggtctttat atgatccagt tttgcagaag     540
tatgatgaga ttccagatct atcgcataat tgcccttat ggtgtttag agagatctgt     600
```

-continued

```
cgtcacatat ctggtccatt accagatcgg gcaccttatc tttacttatc tgcaggggta  660
ttctggttaa tgtcaccacg aatgacgtct gcaatccctc cgctactatc cgatcttgtt  720
aatttagcta ttttgcaaca aactgcgggt ttagatccat cattagtgaa attgggagta  780
cagatatgcc ttcatgcagc agctagctca agttattcat ggtttatctt aaagactaag  840
tctatttttc ctcaaaacac gttgcacagt atgtatgaat ctctagaagg gggatactgt  900
cctaatcttg aatggttaga gcctagatca gactataagt tcatgtacat gggagtcatg  960
ccattgtccg ctaagtatgc taggtcggcg ccgtccaatg ataagaaagc gcgggaactt 1020
ggcgagaaat atggactgag ctcagtcgtc ggtgagcttc gtaaacggac aaagacgtat 1080
gttaaacatg actttgcttc agtgaggtac attcgtgacg ctatggcatg tactagcggt 1140
attttcttgg taagaacacc caccgaaacg gtattgcaag aatatacgca gagtccggac 1200
attaaggttc ccattcccca gaaagactgg acaggcccaa taggtgaaat cagaattcta 1260
aaagatacaa caagttccat cgcgcgttac ttatatagaa catggtactt ggcagcggcg 1320
agaatggcgg ctcaaccacg tacgtgggat ccattgtttc aagcgattat gagatctcaa 1380
tacgtgacag ctaggggtgg atctggcgca gcactccgcg aatctttgta tgcaatcaat 1440
gtgtcgttac ctgatttcaa gggcttacca gtgaaggcag caactaagat attccaggcg 1500
gcacaattag cgaacttgcc gttctcccac acatcagtgg ctatactagc tgacacttca 1560
atgggattgc gaaatcaggt gcagaggcgg ccacgatcca ttatgccatt aaatgtgccc 1620
cagcagcagg tttcggcgcc ccatacattg acagcggatt acattaacta ccacatgaat 1680
ctatcaccca cgtctggtag tgcggtcatt gagaaggtga ttcctttagg tgtatacgct 1740
tcgagccctc ctaaccagtc gatcaacatt gacatatctg cgtgtgacgc tagtattact 1800
tgggatttct ttctgtcagt gattatggcg gctatacacg aaggtgtcgc tagtagctcc 1860
attggaaaac catttatggg ggttcctgca tccattgtaa atgatgagtc tgtcgttgga 1920
gtgagagctg ctaggccgat atcgggaatg cagaacatga ttcagcatct atcgaaacta 1980
tataaacgtg gattttcata tagagtaaac gattcttttt ctccaggtaa cgattttact 2040
catatgacta ccactttccc gtcaggttca acagccacct ctactgagca tactgctaat 2100
aatagtacga tgatggaaac tttcctgaca gtatggggac ccgaacatac tgacgaccct 2160
gacgtcttac gtttaatgaa gtctttaact attcaaagga attacgtatg tcaaggtgat 2220
gatgattaa tgattatcga tgggactact gctggtaagg tgaacagtga aactattcag 2280
aacgatctag aattaatctc aaaatatggt gaggaattcg gatggaaata tgacatagcg 2340
tacgatggga ctgccgaata cttaaagcta tacttcatat ttggctgtcg aattccaaat 2400
cttagtcgcc atccaatcgt ggggaaagaa cgggcgaatt cttcagcaga ggagccatgg 2460
ccagcaattc tagatcagat tatgggtgtc ttctttaatg gtgttcatga tgggttacag 2520
tggcagcggt ggatacgtta ttcatgggct ctatgctgtg ctttctcacg tcaaagaaca 2580
atgattggtg agagcgtggg ttaccttcaa tatcctatgt ggtctttgt ctactgggga 2640
ttaccactgg ttaaagcgtt tgggtcagac ccatggatct tttcttggta catgcctact 2700
ggagatctgg gaatgtatag ttggattagc ttgatacgcc ctctgatgac aagatggatg 2760
gtggctaatg gttacgtaac tgacagatgc tcaaccgtat tcgggaacgc agattatcgc 2820
aggtgtttca atgaacttaa actatatcaa ggttattata tggcacaatt gcccaggaat 2880
cctaagaagt ctggacgagc ggcctctcgg gaggtaagga aacaattcac tcaggcatta 2940
tccgactatc taatgcaaaa tccagagctg aagtcacgtg tgctacgtgg tcgtagtgag 3000
tgggagaaat atggagcggg gataattcac aatcctccgt cattattcga tgtgccccat 3060
aaatggtatc agggtgcgca agaggcagca atcgctacga gagaagagct ggcagaaatg 3120
gatgagacat taatgcgcgc tcgaaggcac agctattcga gctttcaa gttattagag 3180
gcgtatctgc tcgtgaaatg gcgaatgtgc gaggcccgcg aaccgtcggt tgatttgcga 3240
ttaccattat gtgcgggtat tgacccatta aactcagatc ctttctcaa gatggtaagc 3300
gttggaccaa tgctccagag tacgagaaag tactttgctc agacactatt catggcaaag 3360
acggtgtcgg gtcttgacgt taacgcgatt gatagcgcgt tattacgact gcgaacatta 3420
ggtgctgata agaaagcatt aacggcgcag ttattaatgg tggggcttca ggagtcagaa 3480
gcggacgcat tggccgggaa gataatgcta caggatgtga atactgtgca attagccaga 3540
gtggttaact tagctgtgcc agatacttgg atgtcgttag actttgactc tatgttcaaa 3600
caccacgtca agctgcttcc caaagatgga cgtcatctaa atactgatat tcctcctcaa 3660
atgggatggt tacgggccat tttacgattc ttaggtgccg gaatggtaat gactgcgact 3720
ggagttgctg tcgacatcta tctgaggat atacatggcg gtggtcggtc acttggacag 3780
agattcatga cttggatgcg acaggaagga cggtcagcgt gagtctacca tgggtcgtgg 3840
tgcgtcaact catc                                                   3854
```

```
SEQ ID NO: 23            moltype = AA  length = 1267
FEATURE                  Location/Qualifiers
source                   1..1267
                         mol_type = protein
                         organism = Reovirus
SEQUENCE: 23
MSSMILTQFG PFIESISGIT DQSNDVFEDA AKAFSMFTRS DVYKALDEIP FSDDAMLPIP   60
PTIYTKPSHD SYYYIDALNR VRRKTYQGPD DVYVPNCSIV ELLEPHETLT SYGRLSEAIE  120
NRAKDGDSQA RIATTYGRIA ESQARQIKAP LEKFVLALLV AEAGGSLYDP VLQKYDEIPD  180
LSHNCPLWCF REICRHISGP LPDRAPYLYL SAGVFWLMSP RMTSAIPPLL SDLVNLAILQ  240
QTAGLDPSLV KLGVQICLHA AASSSYSWFI LKTKSIFPQN TLHSMYESLE GGYCPNLEWL  300
EPRSDYKFMY MGVMPLSAKY ARSAPSNDKK ARELGEKYGL SSVVGELRKR TKTYVKHDFA  360
SVRYIRDAMA CTSGIFLVRT PTETVLQEYT QSPEIKVPIP QKDWTGPIGE IRILKDTTSS  420
IARYLYRTWY LAAARMAAQP RTWDPLFQAI MRSQYVTARG GSGAALRESL YAINVSLPDF  480
KGLPVKAATK IFQAAQLANL PFSHTSVAIL ADTSMGLRNQ VQRRPRSIMP LNVPQQQVSA  540
PHTLTADYIN YHMNLSPTSG SAVIEKVIPL GVYASSPPNQ SINIDISACD ASITWDFFLS  600
VIMAAIHEGV ASSSIGKPFM GVPASIVNDE SVVGVRAARP ISGMQNMIQH LSKLYKRGFS  660
YRVNDSFSPG NDFTHMTTTF PSGSTATSTE HTANNSTMME TFLTVWGPEH TDDPDVLRLM  720
KSLTIQRNYV CQGDDGLMII DGTTAGKVNS ETIQNDLELI SKYGEEFGWK YDIAYDGTAE  780
YLKLYFIFGC RIPNLSRHPI VGKERANSSA EEPWPAILDQ IMGVFFNGVH DGLQWQRWIR  840
YSWALCCAFS RQRTMIGESV GYLQYPMWSF VYWGLPLVKA FGSDPWIFSW YMPTGDLGMY  900
SWISLIRPLM TRWMVANGYV TDRCSTVFGN ADYRRCFNEL KLYQGYYMAQ LPRNPKKSGR  960
AASREVREQF TQALSDYLMQ NPELKSRVLR GRSEWEKYGA GIIHNPPSLF DVPHKWYQGA 1020
```

```
QEAAIATREE LAEMDETLMR ARRHSYSSFS KLLEAYLLVK WRMCEAREPS VDLRLPLCAG  1080
IDPLNSDPFL KMVSVGPMLQ STRKYFAQTL FMAKTVSGLD VNAIDSALLR LRTLGADKKA  1140
LTAQLLMVGL QESEADALAG KIMLQDVNTV QLARVVNLAV PDTWMSLDFD SMFKHHVKLL  1200
PKDGRHLNTD IPPRMGWLRA ILRFLGAGMV MTATGVAVDI YLEDIHGGGR SLGQRFMTWM  1260
RQEGRSA                                                           1267

SEQ ID NO: 24            moltype = DNA   length = 1196
FEATURE                  Location/Qualifiers
source                   1..1196
                         mol_type = genomic DNA
                         organism = Reovirus
SEQUENCE: 24
gctatttttg cctcttccca gacgttgtcg caatggaggt gtgcttgccc aacggtcatc   60
aggtcgtgga cttgattaac aacgcttttg aaggtcgtgt atcaatctac agcgcgcaag  120
agggatggga caaaacaatc tcagcacagc cagatatgat ggtatgtggt ggcgccgtcg  180
tttgcatgca ttgtctaggt gttgttggat ctctacaacg caagctgaag catttgcctc  240
accatagatg taatcaacag atccgtcatc aggattacgt cgatgtacag ttcgcagacc  300
gtgttactgc tcactggaag cggggtatgc tgtccttcgt tgcgcagatg cacgagatga  360
tgaatgacgt gtcgccagat gacctggatc gtgtgcgtac tgagggaggt tcactagtgg  420
agctgaaccg gcttcaggtt gacccaaatt caatgtttag atcaatacac tcaagttgga  480
cagatccttt gcaggtggtg gacgaccttg acactaagct ggatcagtac tggacagcct  540
taaacctgat gatcgactca tccgacttga tacccaactt tatgatgaga gacccatcac  600
acgcgttcaa tggtgtgaaa ctggaggagg atgctcgtca aacccaattc tccaggactt  660
ttgattcgag atcgagtttg gaatggggtg tgatggttta tgattactct gagctggagc  720
atgatccatc gaagggccgt gcttacgaaa aggaattggt gacgccagct cgagatttcg  780
gtcactttgg attatcccat tattctaggt cgactacccc aatccttgaa aagatgccgg  840
ccgtattctc aggaatgttg actgggaact gtaaaatgta tccattcatt aaaggaacgg  900
ctaagctgaa gacagtgcgc aagctagtgg aggcagtcaa tcatgcttgg ggtgtcgaga  960
agattagata tgctcttggg ccaggtggca tgacgggatg gtacaatagg actatgcaac 1020
aggcccccat tgtgctaact cctgctgctc tcacaatgtt cccagatacc atcaagtttg 1080
gggatttgaa ttatccagtg atgattggcg atccgatgat tcttggctaa acacccccat 1140
cttcacagcg ccgggcttga ccaacctggt gtgacgtggg acaggcttca ttcatc      1196

SEQ ID NO: 25            moltype = AA   length = 365
FEATURE                  Location/Qualifiers
source                   1..365
                         mol_type = protein
                         organism = Reovirus
SEQUENCE: 25
MEVCLPNGHQ VVDLINNAFE GRVSIYSAQE GWDKTISAQP DMMVCGGAVV CMHCLGVVGS   60
LQRKLKHLPH HRCNQQIRHQ DYVDVQFADR VTAHWKRGML SFVAQMHEMM NDVSPDDLDR  120
VRTEGGSLVE LNRLQVDPNS MFRSIHSSWT DPLQVVDDLD TKLDQYWTAL NLMIDSSDLI  180
PNFMMRDPSH AFNGVKLEGD ARQTQFSRTF DSRSSLEWGV MVYDYSELEH DPSKGRAYRK  240
ELVTPARDFG HFGLSHYSRA TTPILGKMPA VFSGMLTGNC KMYPFIKGTA KLKTVRKLVE  300
AVNHAWGVEK IRYALGPGGM TGWYNRTMQQ APIVLTPAAL TMFPDTIKFG DLNYPVMIGD  360
PMILG                                                             365

SEQ ID NO: 26            moltype = DNA   length = 2203
FEATURE                  Location/Qualifiers
source                   1..2203
                         mol_type = genomic DNA
                         organism = Reovirus
SEQUENCE: 26
gctaatctgc tgaccgttac tctgcaaaga tggggaacgc ttcctctatc gttcagacga   60
tcaacgtcac tggagatggc aatgtattta aaccatcagc tgaaacttca tctaccgctg  120
taccatcgtt aagcttatca cctggaatgc tgaatcccgg aggggtacca tggattgctg  180
ttggagatga gacatctgtg acttcaccag gcgcattacg tcgaatgacg tcaaaggaca  240
tcccggaaac ggcaataatc aacacagaca attcatcagg cgccgtgcca agcgaatcag  300
cgcttgtgcc ctacatcgat gagccgctgg tagtggttac agagcatgct attaccaact  360
tcaccaaagc tgagatggca cttgaattca atcgtgagtt ccttgacaag atgcgtgtgc  420
tgtcagtgtc accaaaatat tcggatcttc tgacctatgt tgactgctac gtcggtgtgt  480
ctgctcgtca ggctttaaac aattttcaga aacaagtgcc tgtgattaca cctactaggc  540
agacgatgta tgtcgactcg atacaagcgg ccttgaaagc tttagaaaag tgggagattg  600
atctgagagt ggctcaaacg ttgctgccta cgaacgttcc gattggagaa gtctcttgtc  660
caatgcagtc ggtagtgaaa ctgctggatg atcagctgcc agatgacacg ctgatacgaa  720
ggtatcccaa ggaagccgcc gtcgctttgg ctaaacgaaa cgggggaata caatgcgatg  780
acgtatcaga aggcaccgtg atgaacgagg ctgtcaacgc tgttgcagct agtgcactgg  840
caccttcagc atcagcccca cccttagaag agaagtcaaa gttaaccgaa caagcgatgg  900
atctcgtgac cgcggctgag cctgagataa ttgcctcact cgcgccagtt cccgcacccg  960
tgtttgccat accacctaaa ccagcagatt ataatgtgcg tactctgagg atcgacgagg 1020
ccacttggct gcgaatgatt ccaaaatcaa tgaacacacc ttttcaaatc caggtgactg 1080
ataacacagg aactaattgg catctcaatt tgaggggggg gactcgtgta gtgaatctgg 1140
accaaatcgc tccgatgcgg tttgtattag atttaggggg aaagagttat aaagagacga 1200
gctgtgtaca aacggcaag aaggtcggat tcatcgtttt tcaatcgaag ataccattcg 1260
aactttggac tgctgcttca cagatcggtc aagccacggt ggttaactat gtccaactat 1320
acgctgaaga cagctcattt accgcgcagt ctatcattgc tactacctct ttggcttata 1380
actatgagct gagcagttg aataagactg accctgagat gaattattat cttttggcga 1440
cctttataga ctcagccgct ataacgccaa cgaatatgac acagcctgat gtttgggatg 1500
ccttgctgac gatgtcccca ctatcagctg gcgaggtgac agtgaagggt gcggtagtga 1560
```

-continued

```
gtgaagtagt ccctgcagac ttgataggta gctacactcc agaatcccta aacgcctcac   1620
ttccgaatga tgctgctaga tgcatgatcg atagagcttc gaagatagcc gaagcaatca   1680
agattgatga tgatgctgga ccagatgaat attccccaaa ctctgtacca attcaaggtc   1740
agcttgctat ctcgcaactc gaaactggat atggtgtgcg aatattcaac cctaaaggga   1800
tcctttctaa aattgcatct agggcaatgc aggctttcat tggtgacccg agcacaatca   1860
tcacgcaggc ggcgccagtg ttatcagaca agaataattg gattgcattg gcacaggag    1920
tgaaaactag tctgcgtact aaaagtctat cagcgggagt gaagactgca gtgagtaagc   1980
tgagctcatc tgagtctatc cagaattgga ctcaaggatt cttggataaa gtgtcagcgc   2040
attttccagc accaaagccc gattgtccga ctagcggaga tagtggtgaa tcgtctaatc   2100
gccgagtgaa gcgcgactca tacgcaggag tggtcaaacg tgggtacaca cgttaggccg   2160
ctcgccctgg tgacgcgggg ttaagggatg caggcaaatc atc                     2203
```

```
SEQ ID NO: 27        moltype = AA  length = 708
FEATURE              Location/Qualifiers
source               1..708
                     mol_type = protein
                     organism = Reovirus
SEQUENCE: 27
MGNASSIVQT INVTGDGNVF KPSAETSSTA VPSLSLSPGM LNPGGVPWIA VGDETSVTSP   60
GALRRMTSKD IPETAIINTD NSSGAVPSES ALVPYIDEPL VVVTEHAITN FTKAEMALEF  120
NREFLDKMRV LSVSPKYSDL LTYVDCYVGV SARQALNNFQ KQVPVITPTR QTMYVDSIQA  180
ALKALEKWEI DLRVAQTLLP TNVPIGEVSC PMQSVVKLLD DQLPDDTLIR RYPKEAAVAL  240
AKRNGGIQWM DVSEGTVMNE AVNAVAASAL APSASAPPLE EKSKLTEQAM DLVTAAEPEI  300
IASLAPVPAP VFAIPPKPAD YNVRTLRIDE ATWLRMIPKS MNTPFQIQVT DNTGTNWHLN  360
LRGGTRVVNL DQIAPMRFVL DLGGKSYKET SWDPNGKKVG FIVFQSKIPF ELWTAASQIG  420
QATVVNYVQL YAEDSSFTAQ SIIATTSLAY NYEPEQLNKT DPEMNYYLLA TFIDSAAITP  480
TNMTQPDVWD ALLTMSPLSA GEVTVKGAVV SEVVPADLIG SYTPESLNAS LPNDAARCMI  540
DRASKIAEAI KIDDDAGPDE YSPNSVPIQG QLAISQLETG YGVRIFNPKG ILSKIASRAM  600
QAFIGDPSTI ITQAAPVLSD KNNWIALAQG VKTSLRTKSL SAGVKTAVSK LSSSESIQNW  660
TQGFLDKVSA HFPAPKPDCP TSGDSGESSN RRVKRDSYAG VVKRGYTR              708
```

```
SEQ ID NO: 28        moltype = DNA  length = 2304
FEATURE              Location/Qualifiers
source               1..2304
                     mol_type = genomic DNA
                     organism = Reovirus
SEQUENCE: 28
gctattcgcg gtcatggctt acatcgcagt tcctgcggtg gtggattcac gttcgagtga   60
ggctattgga ctgctagaat cgtttggagt agacgcgggt gctgacgcga atgacgtttc  120
atatcaagat catgactatg tgttggatca gttacagtac atgttagatg gatatgaggc  180
tggtgacgtt atcgatgcac tcgtccacaa gaattggtta catcactctg tctattgctt  240
gttgccaccc aaaagtcaac tattagagta ttggaaaagt aatccttcag cgataccgga  300
caacgttgat cgtcggcttc gtaaacgact aatgctaaag aaagatctca ggaaagatga  360
tgaatacaat cagctagcgc gtgctttcaa gatatcggat gtctacgcac ctctcatctc  420
atccacgacg tcaccgatga caatgataca gaacttgaat cgaggcgaga tcgtgtacac  480
cacgacggac agggtaatag gggctagaat cttgttatat gctcctagaa agtactatgc  540
gtcaactctg tcatttacta tgactaagtg catcattccg tttggtaaag aggtgggtcg  600
tgttcctcac tctcgattta atgttggcac atttccgtca attgctaccc cgaaatgttt  660
tgtcatgagt ggggttgata ttgagtccat cccaaatgaa tttatcaagt tgtttttacca  720
gcgcgtcaag agtgttcacg ctaacatact aaatgacata tctcctcaga tcgtctctga  780
catgataaac agaaagcgtc tgcgcgttca tactccatca gatcgtcgag ccgcgcagtt  840
gatgcatttg ccttaccatg ttaaacgagg agcgtctcac gtcgacgttt acaaggtgga  900
tgttgtagac atgttgttcg aggtagtgga tgtggccgat gggttgcgca acgtatctag  960
gaaactaact atgcataccg ttcctgtatg tattcttgaa atgttgggta ttgagattgc  1020
ggactattgc attcgtcaag aggatggaat gctcacagat tggttcctac ttttaaccat  1080
gctatctgat ggcttgactg atagaaggac gcattgtcaa tacttgatga atccgtcaag  1140
tgtgcctcct gatgtgatac ttaacatctc aattactgga tttataaata gacatacaat  1200
cgatgtcatg cctgacatat atgacttcgt taaacccatt ggcgctgtgc tgcctaaggg  1260
atcatttaaa tcaacaatta tgagaggttct tgattcaata tcaatattag gaatccaaat  1320
catgccgcgc gcgcatgtag ttgactcaga tgaggtgggc gagcaaatgg agcctacgtt  1380
tgagcaggcg gttatggaga tatacaaagg gattgctggc gttgactcgc tggatgatct  1440
catcaagtgg gtgttgaact cggatctcat tccgcatgat gacaggcttg gtcaattatt  1500
tcaagcgttt ttgcctctcg caaaggactt attagctcca atggccagaa agttttatga  1560
taactcaatg agtgagggta gattgctaac attcgctcat gccgacagtg agttgctgaa  1620
cgcaaattat tttggtcatt tattgcgact aaaaatacca tatattcag aggttaatct  1680
gatgattcgc aagaatcgtg agggtggaga gctatttcag cttgtgttat cttatctata  1740
taaaatgtat gctactagcg cgcagcctaa atggtttgga tcattattgc gattgttaat  1800
atgtccctg ttacatatgg agaaattaat aggagaagca gacccggcat ctacgtcggc  1860
tgaaattggg tggcatatcc ctcgtgaaca gctgatgcaa gatgatggt gtggatgtga  1920
agacggattc attccctatg ttagcatacg tgcgccaaga ctggttatag aggagttgat  1980
ggagaagaac tggggccaat atcatgccca agttattgtc actgatcagc ttgtcgtagg  2040
cgaaccgcgc agggtatctg ctaaggctgt gatcaagggt aaccacttac cagttaagtt  2100
agtttcacga tttgcatgtt tcacattgac ggcgaagtat gagatgaggc tttcgtgcgg  2160
ccatagcact ggacgtggag ctgcatacag tgcgagacta gcttccgat ctgacttggc  2220
gtgatccgtg acatgcgtag tgtgacacct gctcctaggt caatgggggt aggggcggg   2280
ctaagactac gtacgcgctt catc                                          2304
```

```
SEQ ID NO: 29        moltype = AA  length = 736
FEATURE              Location/Qualifiers
```

-continued

```
source                  1..736
                        mol_type = protein
                        organism = Reovirus
SEQUENCE: 29
MAYIAVPAVV DSRSSEAIGL LESFGVDAGA DANDVSYQDH DYVLDQLQYM LDGYEAGDVI    60
DALVHKNWLH HSVYCLLPPK SQLLEYWKSN PSAIPDNVDR RLRKRLMLKK DLRKDDEYNQ   120
LARAFKISDV YAPLISSTTS PMTMIQNLNR GEIVYTTTDR VIGARILLYA PRKYYASTLS   180
FTMTKCIIPF GKEVGRVPHS RFNVGTFPSI ATPKCFVMSG VDIESIPNEF IKLFYQRVKS   240
VHANILNDIS PQIVSDMINR KRLRVHTPSD RRAAQLMHLP YHVKRGASHV DVYKVDVVDM   300
LFEVVDVADG LRNVSRKLTM HTVPVCILEM LGIEIADYCI RQEDGMLTDW FLLLTMLSDG   360
LTDRRTHCQY LMNPSSVPPD VILNISITGF INRHTIDVMP DIYDFVKPIG AVLPKGSFKS   420
TIMRVLDSIS ILGIQIMPRA HVVDSDEVGE QMEPTFEQAV MEIYKGIAGV DSLDDLIKWV   480
LNSDLIPHDD RLGQLFQAFL PLAKDLLAPM ARKFYDNSMS EGRLLTFAHA DSELLNANYF   540
GHLLRLKIPY ITEVNLMIRK NREGGELFQL VLSYLYKMYA TSAQPKWFGS LLRLLICPWL   600
HMEKLIGEAD PASTSAEIGW HIPREQLMQD GWCGCEDGFI PYVSIRAPRL VIEELMEKNW   660
GQYHAQVIVT DQLVVGEPRR VSAKAVIKGN HLPVKLVSRF ACFTLTAKYE MRLSCGHSTG   720
RGAAYSARLA FRSDLA                                                  736

SEQ ID NO: 30           moltype = AA   length = 418
FEATURE                 Location/Qualifiers
source                  1..418
                        mol_type = protein
                        organism = Reovirus
SEQUENCE: 30
MARAAFLFKT VGFGGLQNVP INDELSSHLL RAGNSPWQLT QFLDWISLGR GLATSALVPT    60
AGSRYYQMSC LLSGTLQIPF RPNHRWGDIR FLRLVWSAPT LDGLVVAPPQ VLAQPALQAQ   120
ADRVYDCDDY PFLARDPRFK HRVYQQLSAV TLLNLTGFGP ISYVRVDEDM WSGDVNQLLM   180
NYFGHTFAEI AYTLCQASAN RPWEYDGTYA RMTQIVLSLF WLSYVGVIHQ QNTYRTFYFQ   240
CNRRGDAAEV WILSCSLNHS AQIRPGNRSL FVMPTSPDWN MDVNLILSST LTGCLCSGSQ   300
LPLIDNNSVP AVSRNIHGWT GRAGNQLHGF QVRRMVTEFC DRLRRDGVMT QAQQNQVEAL   360
ADQTQQFKRD KLETWAREDD QYNQAHPNST MFRTKPFTNA QWGRGNTGAT SAAIAALI    418
```

VIRAL EXTRACTION FROM CELL CULTURE

CROSS-REFERENCE TO RELATED APPLICATION(S)

This application is a bypass continuation of International Application No. PCT/IB2024/053862, filed Apr. 19, 2024, which claims the benefit of priority of U.S. Provisional Application No. 63/461,216, filed Apr. 21, 2023, the contents of each of which are herein incorporated by reference in their entireties.

REFERENCE TO AN ELECTRONIC SEQUENCE LISTING

The contents of the electronic sequence listing (2024-013-02_SL.xml; Size: 71,043 bytes; and Date of Creation: Apr. 16, 2024) is herein incorporated by reference in its entirety.

BACKGROUND

Triton™ X-100 (polyethylene glycol p-(1,1,3,3-tetramethylbutyl)-phenyl ether) was added to Registration, Evaluation, Authorization and restriction of chemicals (REACH) list in December of 2012 and the REACH Annex XIV sunset date was Jan. 2, 2021. After this date, Triton™ X-100 cannot be used for commercial production in the European Union due to its environmental impact. Therefore, alternative detergent needs to be identified to replace the use of Triton™ X-100 in the manufacture of viral drug products.

BRIEF SUMMARY

Provided herein are methods of producing virus from a culture of host cells. The methods include providing a culture of host cells which has been infected by the virus; contacting the host cells with a first buffer comprising a detergent and incubating the host cells in the presence of the first buffer for a first period of time thereby producing a cell lysate; contacting the cell lysate with a second buffer comprising an endonuclease for a second period of time to degrade the host cell nucleic acids; and collecting the virus.

BRIEF DESCRIPTION OF THE DRAWINGS

FIG. 1 shows increasing the Benzonase® concentration lowered the residual HC DNA levels to those obtained with Triton™ X-100 cell lysis.

FIG. 2 shows increasing the Benzonase® concentration lowered the residual HC DNA levels to those obtained with Triton™ X-100 cell lysis for Benzonase® treatment of at least 90 minutes before clarification, for the same extended storage at 2-8° C. post-clarification.

FIG. 3 shows increasing the Benzonase® concentration lowered the residual HC DNA levels to those obtained with Triton™ X-100 cell lysis for the same extended storage at 2-8° C. post-clarification.

DETAILED DESCRIPTION

Figure 1:
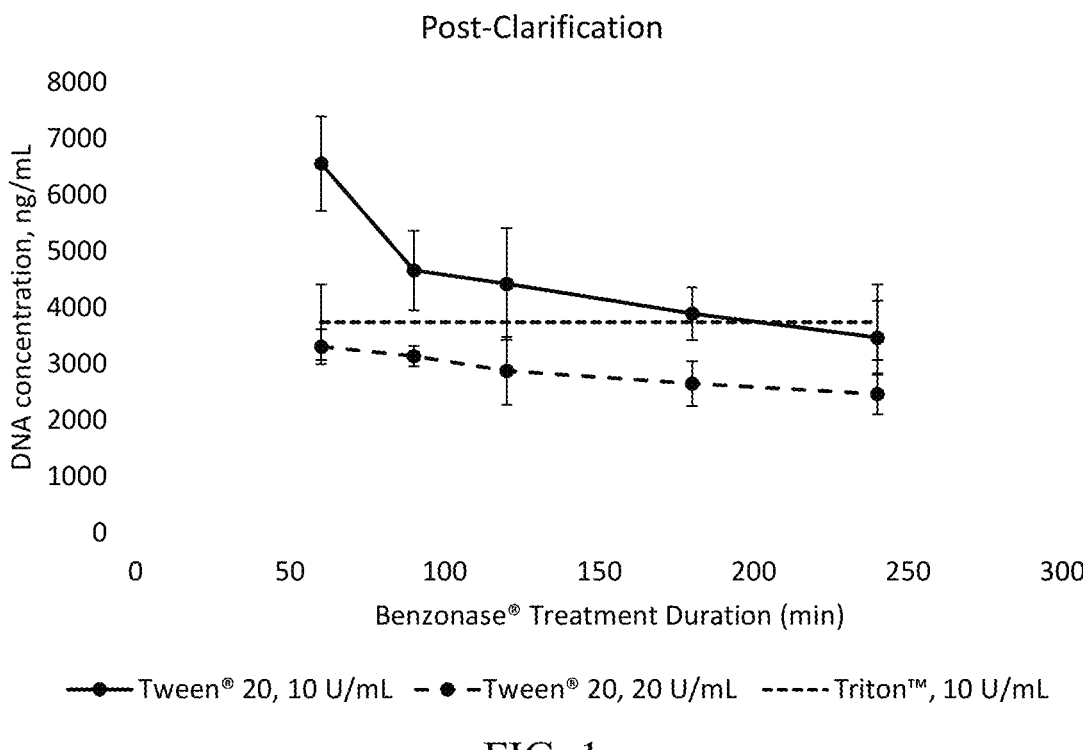
FIG. 1 is a graph showing post-clarification residual host cell (HC) DNA results of testing increasing Benzonase® concentrations from 10 to 20 U/mL and for various durations between 60 to 240 minutes with a cell lysate obtained after a 2 hour incubation of a virus containing cell culture with 1% Tween® 20 and with 20 mM Na$_2$HPO$_4$, pH 8.0.

Due to the vast number of diseases caused by viruses, virology has been an intensively studied field. There has always been the demand to produce viruses efficiently in order to isolate and purify viral proteins, to generate vaccines, or to provide infectious viruses for laboratory studies. Recently, the new development of virus therapy has further necessitated the need for efficient production of infectious viruses.

Described herein is an improved method for the extraction of viruses from cell culture using detergent conditions that can be applied to both small- and large-scale virus production. The method involves an extraction step in which a detergent is added to the cell culture. Thereafter, cell debris can be removed from the extraction mixture by, for example, filtration or centrifugation. The resulting virus suspension can be further concentrated and/or enriched by chromatographic methods. The virus prepared according to the present invention can be used for any purpose, including purification of viral proteins, vaccination, infection of host cells and clinical administration. The methods provided herein are advantageous for the production of viral drug substances, as they result in overall higher yields and the detergents provided herein are a superior replacement to Triton™ X-100. The methods also result in decreased amounts of residual host cell DNA (HC DNA).

As used herein, "adherent cells" refer to cells which adhere to the culture containers in a cell culture. Examples of adherent cells include monolayer cells, which are cells that form a single layer of cells on the surface of a culture container. "Suspension cells" or "suspended cells" refer to cells which do not adhere to culture containers in a cell culture. Suspension cells can be grown in a "spin culture," which is a culture in which the culture medium is stirred continuously during the culture process.

As used herein, "ambient temperature" refers to a temperature between about 10° C. and about 30° C. Ambient temperature is preferably between about 15° C. and about 30° C., more preferably between about 20° C. and about 25° C., and most preferably about 25° C.

As used herein, a virus that is "cell associated" refers to a virus which is attached to or trapped in part of a cell in which the virus has been produced. Thus, a virus is cell associated before the host cell is lysed. When cell lysis begins, a virus may be still attached to or trapped in part of the broken cell and remain cell associated. However, when the virus is released free into the medium, it is not cell associated anymore. A "cell free virus" is a virus which is not cell associated.

As used herein, a "cell culture" or "culture of cells" means a population of cultured cells as found in their culture conditions. In particular, a cell culture includes the cells and the culture medium. Cells that have been pelleted are not considered a cell culture unless they are placed in culture medium under culture conditions again.

As used herein, "cell lysis" refers to the disruption of the cell membrane of a cell and the subsequent release of all or part of the content of the cell.

As used herein, "clinical administration" of a substance refers to contacting any part of the body of a living organism with the substance in order to improve or maintain the organism's health conditions.

As used herein, "collecting" the virus refers to the act of separating the virus produced from a cell culture which has been previously infected with the virus. The virus is typically collected by separating cellular debris from the virus and harvesting the portion which comprises the virus. Optionally, the virus can be further separated from the soluble substances, e.g., by centrifugation.

As used herein, "culture conditions" refer to the conditions used in a cell culture, including but not limited to the temperature, type of culture containers, humidity, concentration of $CO_2$ or any other gas used in the culture containers, type of culture medium, the initial density of the cultured cells, and, if the cells are infected with a virus, the initial multiplicity of infection.

As used herein, "cytopathic effect" is the damage to infected host cells. Cytopathic effect may be indicated by cells becoming swollen and granular in appearance and cell clumps breaking up. Cells which show a cytopathic effect may also take up the staining dye in a viable cell count.

As used herein, a "detergent" is a substance having a hydrophilic moiety and a hydrophobic moiety. The detergent is preferably a synthetic chemical compound and more preferably a biodegradable synthetic chemical compound. A detergent useful in the present invention enhances disruption of cell membranes to facilitate release of the content of the disrupted cells.

As used herein, a cell is "disrupted" when the cell membrane is ruptured and at least some of the cell content is released from the cell. A cell may be disrupted, for example, by freeze-thawing, sonication or detergent treatments.

As used herein, "extracting" a virus refers to the act of converting a cell associated virus into a cell free virus.

As used herein, "HEK 293 cells" refer to the human embryo kidney cell line designated 293 (ATCC Number CRL-1573) or its derivatives. For example, 293/SF cells (ATCC Number CRL-1573.1) are HEK 293 cells which have been adapted to grow in serum-free media. Also contemplated in this invention are HEK 293 cells adapted to grow in other culture conditions, or any kind of HEK 293 cells or derivatives which are transformed with an exogenous DNA, provided that this transformation does not impair the ability of the cells to support efficient reovirus production as described in this invention.

As used herein, "incubating" after addition of a detergent to a cell culture refers to the act of allowing the cell culture to be mixed with the detergent for a period of time.

As used herein, "multiplicity of infection" or "MOI" refer to the ratio of the number of virus to the number of cells when a virus is used to contact cells.

As used herein, a "non-enveloped virus" is a virus which does not have an envelope. For example, a non-enveloped virus may be any virus which belongs to the family of Adenoviridae (e.g., adenovirus), Picornaviridae (e.g., polio virus), Reoviridae (e.g., reovirus), Papovarviridae (e.g., papilloma virus), Parvoviridae (e.g., Kilham rat virus) or Iridoviridae (e.g., tipula iridescent virus).

As used herein, "viability of the cells" or "percentage of cells remaining viable" is the percentage of the cells which do not show a cytopathic effect in a population.

As used herein, "viral infection" refers to the entry of a virus into a cell and the subsequent replication of the virus in the cell.

The term "about", as used herein, may be used to take into account experimental error, measurement error, and variations that would be expected by a person having ordinary skill in the art. For example, "about" may mean plus or minus 10%, or plus or minus 5%, of the indicated value to which reference is being made.

Provided herein is a method of producing virus from a culture of host cells. The methods include providing a culture of host cells which has been infected by the virus and contacting the host cells with a first buffer comprising a detergent and incubating the host cells in the presence of the first buffer for a first period of time thereby producing a cell lysate. The cell lysate is then contacted by a second buffer comprising an endonuclease for a second period of time to degrade the host cell nucleic acids followed by collection of the virus.

The detergent can be a nonionic detergent or an anionic detergent. The nonionic detergent can be Tween® 20 (polysorbate 20), Octyl Beta-D-Glucopyranoside (OGP), Tergitol™ 15-S-9 (C12-14 secondary alcohol ethoxylate, also referred to as polyethylene glycol trimethylnonyl ether) or Tween® 80 (polysorbate 80). The anionic detergent can be sodium deoxycholate. The detergents can be present at a concentration of between 0.5% to 2.0% (v/v) or any amount in between 0.5% and 2.0% (v/v). Thus, for example, the detergent can be at a concentration of 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0% (v/v) in the buffer. Optionally, the detergent is Tween® 20 and is present in the buffer at a concentration of 0.5%, 1.0% or 2.0% (v/v).

In the provided methods, the first buffer containing the detergent can also include a phosphate. The first buffer can contain phosphate, for example, at a concentration of 10 mM to 25 mM phosphate, 10 mM to 20 mM phosphate, 15 mM to 25 mM phosphate, 10 mM to 15 mM phosphate, 15 mM to 20 mM phosphate or any concentration between 10 mM and 25 mM phosphate. Optionally, the first buffer contains phosphate at a concentration of at least 20 mM phosphate. The phosphate can be, for example, sodium phosphate or potassium phosphate.

In the provided methods, the host cells can be incubated in the presence of the first buffer for a period of time. Optionally, the first period of time is 60 minutes, 120 minutes, 180 minutes or 240 minutes. In addition, incubating the host cells in the presence of the first buffer can occur at a pH of 7.0 to 8.0. Optionally, incubating the host cells in the presence of the first buffer occurs at a pH of 8.0. Incubation of the host cells can occur at a particular temperature. For example, incubating the host cells can occur at a temperature of 30° C. to 40° C. Optionally, incubating the host cells occurs at a temperature of 35° C. to 39° C.

Optionally, incubating the host cells occurs at a temperature of 36° C. to 38° C. Optionally, incubating the host cells occurs at a temperature of 37° C.

In the provided methods, contacting of the host cells with the first buffer can occur under agitation conditions. For example, contacting the host cells with the first buffer can occur under agitation at 120 rpm.

In the provided methods, the cell lysate is then contacted by a second buffer comprising an endonuclease for a second period of time to degrade the host cell nucleic acids. Optionally, the second period of time is 60 minutes, 90 minutes, 120 minutes, 180 minutes, or 240 minutes. Optionally, the endonuclease is Benzonase® (a promiscuous, genetically engineered *Serratia marcescens* endonuclease that cleaves all forms of DNA and RNA, including single-stranded, double-stranded, linear, and circular) or DNase I (an endonuclease that cleaves single- and double-stranded DNA). The endonuclease can be contacted with the cell lysate at a concentration of 10 to 20 U/mL or any amount between 10 and 20 U/mL. For example, the concentration of the endonuclease can be 10, 11, 12, 13, 14, 15, 16, 17, 18, 19, or 20 U/mL. The cell lysate can be contacted with the endonuclease at a particular temperature. Optionally, contacting the cell lysate with the endonuclease occurs at a temperature of 30° C. to 40° C. Optionally, contacting the cell lysate with the endonuclease occurs at a temperature of 35° C. to 39° C. Optionally, contacting the cell lysate with the endonuclease occurs at a temperature of 37° C. Optionally, the contacting of the cell lysate with the endonuclease can occur under agitation conditions. For example, the contacting of the cell lysate with the endonuclease can be at 120 rpm.

In the provided methods, the second buffer can include other components. For example, the second buffer can include $MgCl_2$.

The methods provided herein can further include removing cell debris. Optionally, the cell debris is removed by filtration. Thus, the virus can be purified based on, for example, the size or density difference between the virus and the other constituents in the extract. Particularly, filtration or centrifugation can be employed to separate cell debris from the virus. The cell debris can be removed in a single step or using a step-wise filtration protocol. For example, a pre-filter having a relatively large pore size (e.g., 5 μm or 8 μm) can be first used to remove large pieces from the extraction mixture, followed by filters with small pore sizes, such as a combination filter unit containing a 3 μm filter and a 0.8 μm filter. Optionally, after the 5 μm or 8 μm pre-filter step, a filter having a single pore size of 0.8 μm can be used.

In the provided methods, the cells can be mammalian cells. Optionally, the cells are human embryo kidney 293 (HEK 293) cells. Other cells suitable for use in the provided methods include, but are not limited to, mouse L929 cells, African green monkey kidney cells (Vero cells) and Chinese hamster ovary (CHO) cells. The mammalian cells are, optionally, grown in suspension.

The virus can be purified using any means suitable for viral purification. For example, the virus can be purified based on its surface charge. Optionally, the virus can be purified by ion exchange chromatography or by size exclusion chromatography. Optionally, the methods further include purifying the virus by a combination of ion exchange and size exclusion chromatography. Optionally, the ion exchange is performed prior to the size exclusion chromatography. Optionally, the ion exchange is performed after the size exclusion chromatography. The ion exchange can be performed using an anion exchanger. Optionally, a phosphate buffer can be used in the ion exchange and can be, for example, at a concentration of 100 mM sodium phosphate or monosodium phosphate. Optionally, a phosphate buffer is used in the size exclusion chromatography and can be, for example, at a concentration of between 10-15 mM sodium phosphate, e.g., 10, 11, 12, 13, 14, or 15 mM sodium phosphate. Optionally, the size exclusion chromatography is carried out at a pH of 7.0 to 7.5, for example, pH 7.0, 7.1, 7.2, 7.3, 7.4 or 7.5.

The virus may also be purified based on the difference in size, for example, with size exclusion chromatography. Optionally, an anion exchange column can be used prior to size exclusion chromatography. Other chromatographic methods, such as those based on affinity or hydrophobic interaction, can also be used where appropriate.

Also provided herein is a method of producing reovirus that includes providing a culture of HEK 293 cells which has been infected by reovirus; contacting the cells with a first buffer comprising Tween® 20 and a phosphate and incubating the HEK 293 cells in the presence of the first buffer for a first period of time thereby producing a cell lysate, wherein the incubating occurs at a temperature of about 30° C. to about 40° C. and a pH of about 7.0 to about 8.0; contacting the cell lysate with a second buffer comprising an endonuclease for a second period of time to degrade the host cell nucleic acids; removing cell debris by filtration; concentrating the filtrate by ultrafiltration and diafiltration; purifying the reovirus by a combination of ion exchange and size exclusion chromatography; and collecting the reovirus. Optionally, the first buffer comprises 15 mM to 25 mM phosphate. Optionally, the first buffer comprises at least 20 mM phosphate. The phosphate can be, for example, sodium phosphate. Optionally, the first buffer comprises 0.5%, 1.0% or 2.0% (v/v) Tween® 20. The first period of time can be 60 minutes, 120 minutes, 180 minutes or 240 minutes. The second period of time can be 60 minutes, 90 minutes, 120 minutes, 180 minutes, or 240 minutes. The endonuclease can be Benzonase®. The endonuclease can be contacted with the cell lysate at a concentration of 10 to 20 U/mL. Optionally, contacting the cell lysate with the endonuclease occurs at a temperature of 30° C. to 40° C. Optionally, contacting the cell lysate with the endonuclease occurs at a temperature of 35° C. to 39° C. Optionally, contacting the cell lysate with the endonuclease occurs at a temperature of 37° C. Optionally, incubating the host cells occurs at a temperature of 35° C. to 39° C. Optionally, incubating the host cells occurs at a temperature of 37° C. Optionally, incubating the host cells in the presence of the first buffer occurs at a pH of 7.0 to 8.0, or at a pH of 8.0. In these methods, the second buffer can further include $MgCl_2$.

Oncolytic viruses that are used in the provided methods and kits include, but are not limited to, oncolytic viruses that are members in the family of reoviridae, myoviridae, siphoviridae, podoviridae, tectiviridae, corticoviridae, plasmaviridae, lipothrixviridae, fuselloviridae, poxyiridae, iridoviridae, phycodnaviridae, baculoviridae, herpesviridae, adenoviridae, papovaviridae, polydnaviridae, inoviridae, microviridae, geminiviridae, circoviridae, parvoviridae, hepadnaviridae, retroviridae, cystoviridae, birnaviridae, paramyxoviridae, rhabdoviridae, filoviridae, orthomyxoviridae, bunyaviridae, arenaviridae, leviviridae, picornaviridae, sequiviridae, comoviridae, potyviridae, caliciviridae, astroviridae, nodaviridae, tetraviridae, tombusviridae, coronaviridae, flaviviridae, togaviridae, and barnaviridae. Immunoprotected viruses and reassortant or recombinant viruses of these and other oncolytic viruses are also encompassed by the provided methods. Thus, the oncolytic virus used in the provided methods is, for example, selected from the group consisting of a reovirus, a Newcastle disease virus (NDV), a vesicular stomatitis virus (VSV), an adenovirus, a vaccinia virus, a parapox orf virus, a Sindbis virus, and a herpes simplex virus. Furthermore, a combination of at least two oncolytic viruses can also be employed to practice the provided methods. A few oncolytic viruses are discussed below, and a person of ordinary skill in the art can practice the present methods using other oncolytic viruses as well according to the disclosure herein and knowledge available in the art.

The virus used in the provided methods and kits may be a non-enveloped virus. Optionally, the virus is a reovirus, for example, a mammalian reovirus, a human reovirus, a serotype 3 virus, a serotype 3 reovirus of the Dearing strain or a recombinant reovirus.

When a virus enters a cell, double-stranded RNA kinase (PKR) is activated, blocking protein synthesis, and the virus cannot replicate in this cell. Some viruses have developed a system to inhibit PKR and to facilitate viral protein synthesis as well as viral replication. For example, adenovirus makes a large amount of a small RNA, VA1 RNA. VA1 RNA has extensive secondary structures and binds to PKR in competition with the double-stranded RNA (dsRNA) that normally activates PKR. Since a minimum length of dsRNA is required to activate PKR, VA1 RNA does not activate PKR. Instead, it sequesters PKR by virtue of its large amount. Consequently, protein synthesis is not blocked, and adenovirus can replicate in the cell. Accordingly, if the PKR inhibitors in adenovirus, vaccinia virus, herpes simplex virus, or parapox orf virus are mutated so as not to block PKR function anymore, the resulting viruses do not infect normal cells due to protein synthesis inhibition by PKR, but they replicate in cancer cells lacking PKR activities. Optionally, the oncolytic virus is an adenovirus mutated in the VA1 region, a vaccinia virus mutated in the K3L and/or E3L region, a vaccinia virus mutated in the thymidine kinase (TK) gene, a vaccinia virus mutated in the vaccinia growth factor (VGF) gene, a herpes virus mutated in the 7134.5 gene, a parapox orf virus mutated in the OV20.0L gene, or an influenza virus mutated in the NS-1 gene.

Vaccinia viruses mutated in the viral thymidine kinase (TK) gene are unable to make nucleotides needed for DNA replication. In normal cells, the cellular TK levels are usually very low and the virus is unable to replicate. In tumors, loss of the tumor suppressor Rb or an increase in cyclin activity leads to E2F pathway activation and high levels of TK expression. Thus, cancer cells have high TK levels and the mutated vaccinia virus can replicate and spread.

The vaccinia growth factor (VGF) gene is a homolog of mammalian epidermal growth factor (EGF) and can bind and activate the EGF Receptor (EGFR). Vaccinia viruses mutated in the VGF gene are growth restricted to cells with activated EGF pathways, which is commonly mutated in cancers.

The viruses can be modified or mutated according to the known structure-function relationship of the viral PKR inhibitors. For example, since the amino terminal region of E3 protein interacts with the carboxy-terminal region domain of PKR, deletion or point mutation of the carboxy-terminal region domain prevents anti-PKR function (Chang et al., PNAS 89:4825-4829 (1992); Chang et al., Virology 194:537-547 (1993); Chang et al., J. Virol. 69:6605-6608 (1995); Sharp et al., Virol. 250:301-315 (1998); and Romano et al., Mol. and Cell. Bio. 18:7304-7316 (1998)). The K3L gene of vaccinia virus encodes pK3, a pseudosubstrate of PKR. Truncations or point mutations within the C-terminal portion of K3L protein that is homologous to residues 79 to 83 in eIF-2 abolish PKR inhibitory activity (Kawagishi-Kobayashi et al., Mol. Cell. Biology 17:4146-4158 (1997)).

Another example is the Delta24 virus, which is a mutant adenovirus carrying a 24 base pair deletion in the E1A region. (Fueyo et al., Oncogene 19(1):2-12 (2000)). This region is responsible for binding to the cellular tumor suppressor Rb and inhibiting Rb function, thereby allowing the cellular proliferative machinery, and hence virus replication, to proceed in an uncontrolled fashion. Delta24 has a deletion in the Rb binding region and does not bind to Rb. Therefore, replication of the mutant virus is inhibited by Rb in a normal cell. However, if Rb is inactivated and the cell becomes neoplastic, Delta24 is no longer inhibited. Instead, the mutant virus replicates efficiently and lyses the Rb-deficient cell.

In addition, vesicular stomatitis virus (VSV) selectively kills neoplastic cells. A herpes simplex virus 1 (HSV-1) mutant defective in ribonucleotide reductase expression, hrR3, replicates in colon carcinoma cells but not normal liver cells (Yoon et al., FASEB J. 14:301-311(2000)). Newcastle disease virus (NDV) replicates preferentially in malignant cells, and the most commonly used strain is 73-T (Reichard et al., J. Surgical Research 52:448-453 (1992); Zorn et al., Cancer Biotherapy 9(3):22-235 (1994); Bar-Eli et al., J. Cancer Res. Clin. Oncol. 122: 409-415 (1996)). Vaccinia virus propagates in several malignant tumor cell lines. Encephalitis virus has an oncolytic effect in a mouse sarcoma tumor, but attenuation may be required to reduce its infectivity in normal cells. Tumor regression has been described in tumor patients infected with herpes zoster, hepatitis virus, influenza, varicella, and measles virus (for a review, see Nemunaitis, J. Invest. New Drugs 17:375-386 (1999)).

Optionally, the oncolytic virus is a modified, non-reovirus virus comprising a reovirus sigma 1 protein, wherein the reovirus sigma 1 protein replaces the native attachment protein of the non-reovirus virus and wherein the modified virus does not comprise any portion of the native attachment protein of the non-reovirus virus. In the modified, non-reovirus virus, the reovirus sigma 1 protein attaches to carrier cells that protect the virus from neutralizing antibodies during in vivo delivery to a tumor, for example, during systemic delivery. The non-reovirus virus can be, but is not limited to, an adenovirus, a vaccinia virus, a herpes simplex virus, a Sindbis virus, or a parapox virus. Optionally, the full-length sequence of the native attachment protein of the non-reovirus virus is replaced with a reovirus sigma 1 protein. Replacement of the native attachment protein of the virus with a reovirus sigma 1 protein allows the virus to attach to carrier cells which protect the virus from neutralizing antibodies during in vivo delivery. The reovirus sigma-1 protein is described in, for example, WO 2008/11004, which is incorporated by reference herein in its entirety.

Optionally, the oncolytic virus is a reovirus. Reovirus refers to any virus classified in the reovirus genus, whether naturally occurring, modified, or recombinant. Reoviruses are viruses with a double-stranded, segmented RNA genome. The virions measure 60-80 nm in diameter and possess two concentric capsid shells, each of which is icosahedral. The genome consists of double-stranded RNA in 10-12 discrete segments with a total genome size of 16-27 kbp. The individual RNA segments vary in size. Three distinct but related types of reoviruses have been recovered from many species. Thus, the reovirus can be a mammalian reovirus or a human reovirus. All three types share a common complement-fixing antigen.

Human reovirus includes three serotypes: type 1 (strain Lang or T1L), type 2 (strain Jones, T2J), and type 3 (strain Dearing or strain Abney, T3D). The three serotypes are easily identifiable on the basis of neutralization and hemag-glutinin-inhibition assays. A reovirus according to this dis-closure can be a type 3 mammalian orthoreovirus. Type 3 mammalian orthoreoviruses include, without limitation, Dearing and Abney strains (T3D or T3A, respectively). See, for example, ATCC Accession Nos. VR-232 and VR-824. See, for example, U.S. Pat. Nos. 6,110,461; 6,136,307; 6,261,555; 6,344,195; 6,576,234; and 6,811,775, which are incorporated by reference herein in their entireties.

Optionally, the provided methods include the use of reoviruses with mutations. For example, mutant reoviruses as described herein can contain a mutation that reduces or essentially eliminates expression of a sigma3 polypeptide or that results in the absence of a functional sigma3 polypep-tide as described in U.S. Publication No. 2008/0292594, which is incorporated by reference herein in its entirety. A mutation that eliminates expression of a sigma3 polypeptide or that results in the absence of a functional sigma3 poly-peptide can be in the nucleic acid encoding the sigma3 polypeptide (i.e., the S4 gene) or in a nucleic acid that encodes a polypeptide that regulates the expression or function of the sigma3 polypeptide.

As used herein, a mutation that reduces the expression of a sigma3 polypeptide refers to a mutation that results in a decrease in the amount of sigma3 polypeptide, compared to a reovirus expressing wild type levels of sigma3 polypep-tide, of at least 30% (e.g., at least 40%, at least 50%, at least 60%, at least 70%, at least 80%, at least 90%, or at least 95%). As used herein, a mutation that essentially eliminates expression of a sigma3 polypeptide refers to a mutation that results in a decrease in the amount of sigma3 polypeptides, relative to the amount of sigma3 polypeptides produced by a wild type reovirus, of at least 95% (e.g., at least 96%, at least 97%, at least 98%, at least 99%, or 100%). As used herein, a mutation that results in a decrease in or absence of a functional sigma3 polypeptide refers to a mutation that allows expression of the sigma3 polypeptide but that results in a sigma3 polypeptide that is not able to assemble or incorporate into the viral capsid. It would be understood that it may be desirable or necessary for sigma3 polypeptides to retain other functionalities (e.g., the ability to bind RNA) in order for the mutant reovirus to retain the ability to propa-gate.

A mutation in a sigma3 polypeptide as described herein can result in a sigma3 polypeptide that is incorporated into the capsid at levels that are reduced relative to a sigma3 polypeptide that does not contain the mutation (e.g., a wild type sigma3 polypeptide). A mutation in a sigma3 polypep-tide as described herein also can result in a sigma3 poly-peptide that cannot be incorporated into a viral capsid. Without being bound by any particular mechanism, a sigma3 polypeptide may have reduced function or lack function due, for example, to an inability of the sigma3 polypeptide and the mu1 polypeptide to bind appropriately, or due to a conformational change that reduces or prohibits incorpora-tion of the sigma3 polypeptide into the capsid.

In addition to a mutation that abolishes or reduces expres-sion of the sigma3 polypeptide or that results in a non-functional or reduced-function sigma3 polypeptide, a mutant reovirus as described herein may contain one or more further mutations (e.g., a second, third, or fourth mutation) in one of the other reovirus capsid polypeptides (e.g., mu1, lambda2, and/or sigma1). Reoviruses containing a mutation affecting the sigma3 polypeptide and, optionally, a further mutation in any or all of the other outer capsid proteins can be screened for the ability of such mutant reoviruses to infect and cause lysis of cells. For example, neoplastic cells that are resistant to lysis by wild type reovirus can be used to screen for effective mutant reoviruses described herein.

For example, a further mutation can reduce or essentially eliminate expression of a mu1 polypeptide or result in the absence of a functional mu1 polypeptide. The mu1 poly-peptide, which is encoded by the M2 gene, is likely involved in cell penetration and may play a role in transcriptase activation. Each virion contains about 600 copies of mu1 polypeptide, which are present in the form of 1:1 complexes with sigma3 polypeptides. The mu1 polypeptide is myris-toylated on its N-terminus, and then the myristoylated N-terminal 42 residues are cleaved off, resulting in a C-ter-minal fragment (mu1C). Additionally, or alternatively, a further mutation can reduce or essentially eliminate expres-sion of a lambda2 polypeptide or result in the absence of a functional lambda2 polypeptide, and/or a further mutation can reduce or essentially eliminate expression of a sigma1 polypeptide or result in the absence of a functional sigma1 polypeptide. The lambda2 polypeptide is encoded by the L2 gene, is involved in particle assembly, and exhibits guany-lyltransferase and methyltransferase activity. The sigma1 polypeptide is encoded by the S1 gene, is involved in cell-attachment and serves as the viral hemagglutinin.

Optionally, the reovirus comprises a lambda-3 polypep-tide having one or more amino acid modifications, a sigma-3 polypeptide having one or more amino acid modifications, a mu-1 polypeptide having one or more amino acid modifi-cations, a mu-2 polypeptide having one or more amino acid modifications, or any combination thereof. For example, the reovirus has a lambda-3 polypeptide having one or more amino acid modifications; a sigma-3 polypeptide having one or more amino acid modifications; a mu-1 polypeptide having one or more amino acid modifications; and/or a mu-2 polypeptide having one or more amino acid modifications, as described in U.S. Ser. No. 12/046,095, which is incorpo-rated by reference herein in its entirety. By way of example, the one or more amino acid modifications in the lambda-3 polypeptide are a Val at residue 214, an Ala at residue 267, a Thr at residue 557, a Lys at residue 755, a Met at residue 756, a Pro at residue 926, a Pro at residue 963, a Leu at residue 979, an Arg at residue 1045, a Val at residue 1071, or any combination thereof, numbered relative to GenBank Accession No. M24734.1 (SEQ ID NO:23). It is noted that, when the amino acid sequence is a Val at residue 214 or a Val at residue 1071, the amino acid sequence further includes at least one additional change in the amino acid sequence. Optionally, the lambda-3 polypeptide includes the sequence shown in SEQ ID NO:19. Further by way of example, the one or more amino acid modifications in the sigma-3 polypeptide are a Leu at residue 14, a Lys at residue 198, or any combination thereof, numbered relative to GenBank Accession No. K02739 (SEQ ID NO:25). It is noted that, when the amino acid sequence is a Leu at residue 14, the amino acid sequence further includes at least one additional change in the amino acid sequence. Optionally, the sigma-3 polypeptide includes the sequence shown in SEQ ID NO:15. Further by way of example, the one or more amino acid modifications in the mu-1 polypeptide is an Asp at residue 73 numbered relative to GenBank Accession No. M20161.1 (SEQ ID NO:27). Optionally, the mu-1 polypep-tide includes the sequence shown in SEQ ID NO: 17. Also by way of example, the amino acid modification mu-2 polypeptide is a Ser at residue 528 numbered relative to GenBank Accession No. AF461684.1 (SEQ ID NO:29). Optionally, the mu-1 polypeptide includes the sequence shown in SEQ ID NO:17. A reovirus as described herein having one or more modifications can further include a reovirus sigma-2 polypeptide. Such a sigma-2 polypeptide has a Cys at one or more of position 70, 127, 195, 241, 255, 294, 296, or 340, numbered relative to GenBank Accession No. NP_694684.1 (SEQ ID NO:30). Optionally, the sigma-2 polypeptide includes the sequence shown in SEQ ID NO: 12.

Optionally, the reovirus comprises a L1 genome segment comprising one or more nucleic acid modifications, an S4 genome segment comprising one or more nucleic acid modifications, an M1 genome segment comprising one or more nucleic acid modifications, an M2 genome segment comprising one or more nucleic acid modifications, or any combination thereof. Optionally, the reovirus has a L1 genome segment having one or more nucleic acid modifications; a S4 genome segment having one or more nucleic acid modifications; a M1 genome segment having one or more nucleic acid modifications; and/or a M2 genome segment having one or more nucleic acid modifications, as described in WO 2008/110004, which is incorporated by reference herein in its entirety. By way of example, the one or more nucleic acid modifications in the L1 genome segment are a T at position 660, a G at position 817, an A at position 1687, a G at position 2283, an ATG at positions 2284-2286, a C at position 2794, a C at position 2905, a C at position 2953, an A at position 3153, or a G at position 3231, numbered relative to GenBank Accession No. M24734.1 (SEQ ID NO:22). Optionally, the L1 genome segment includes the sequence shown in SEQ ID NO:8. Further by way of example, the one or more nucleic acid modifications in the S4 genome segment is an A at position 74 and an A at position 624, numbered relative to GenBank Accession No. K02739 (SEQ ID NO:24). Optionally, the S4 genome segment includes the sequence shown in SEQ ID NO:4. Further by way of example, the nucleic acid modification in the M2 genome segment can be a C at position 248, numbered relative to GenBank Accession No. M20161.1 (SEQ ID NO:26). The M2 genome segment, for example, includes the sequence shown in SEQ ID NO:6. Also by way of example, the nucleic acid modification in the M1 genome segment is a T at position 1595, numbered relative to GenBank Accession No. AF461684.1 (SEQ ID NO:28). Optionally, the M1 genome segment includes the sequence shown in SEQ ID NO:5. A reovirus as described herein can include any modification or combination of modifications disclosed herein. Optionally, a reovirus as described herein includes genomic segments having the sequences shown in SEQ ID NOs:1-10 or the polypeptides shown in SEQ ID NOs:11, 12, and 16-21, and either or both of the sequences shown in SEQ ID NO:13 and 14. Optionally, a reovirus as disclosed herein is identified as IDAC Accession No. 190907-01, which was deposited with the International Depositary of Canada (IDAC, National Microbiology Laboratory, Public Health Agency of Canada, 1015 Arlington St., Winnipeg, Manitoba Canada R3E 3R2 on Sep. 19, 2007.

Sindbis virus (SIN) can be used in the methods described herein. Sindbis virus is a member of the alphavirus genus of the togaviridae family. The Sindbis virus genome is a single-stranded RNA of 11703 nucleotides, capped at the 5' terminus and poly-adenylated at the 3' terminus. The genome consists of a 49S untranslated region (UT), non-structural proteins nsP1, nsP2, nsP3, and nsP4 followed by a promoter. The promoter is followed by a 26S UT, structural proteins C, E3, E2, 6K, and E1 and finally a 3' UT and a poly-adenylated terminus. The genomic 49S RNA is of plus sense, is infectious, and serves as mRNA in the infected cell.

Sindbis vectors systemically and specifically infect/detect and kill metastasized tumors in vivo, leading to significant suppression of tumor growth and enhanced survival (Hurtado et al., Rejuvenation Res. 9(1):36-44 (2006)). Sindbis virus infects mammalian cells using the Mr 67,000 laminin receptor, which is elevated in tumor versus normal cells. Tumor overexpression of the laminin receptor may explain the specificity and efficacy that Sindbis vectors demonstrate for tumor cells in vivo. Sindbis does not have to undergo genetic manipulation to target cancer cells or to be injected directly into tumors. Sindbis injected anywhere into a subject travels through the bloodstream to the target area (Tseng et al., Cancer Res. 64(18):6684-92 (2004). Sindbis can also be genetically engineered to carry one or more genes that suppress the immune response to the virus and/or genes that stimulate an immune response against the tumor such as, for example, antitumor cytokine genes such as interleukin-12 and interleukin-15 genes.

The virus may be chemically or biochemically pretreated (e.g., by treatment with a protease, such as chymotrypsin or trypsin) prior to administration to the neoplastic cells. Pretreatment with a protease removes the outer coat or capsid of the virus and may increase the infectivity of the virus. The virus may be coated in a liposome or micelle (Chandran and Nibert, J. of Virology 72(1):467-75 (1998)) to reduce or prevent an immune response from a mammal which has developed immunity to the virus. For example, the virion may be treated with chymotrypsin in the presence of micelle forming concentrations of alkyl sulfate detergents to generate a new infectious subvirion particle. The oncolytic virus may also be a reassortant virus or an ISVP.

The oncolytic virus may be a recombinant oncolytic virus. For example, the recombinant oncolytic virus results from the reassortment of genomic segments from two or more genetically distinct oncolytic viruses, also referred to herein as a reassortant. Reassortment of oncolytic virus genomic segments may occur following infection of a host organism with at least two genetically distinct oncolytic viruses. Recombinant viruses can also be generated in cell culture, for example, by co-infection of permissive host cells with genetically distinct oncolytic viruses. Optionally, the methods include the use of recombinant oncolytic virus resulting from reassortment of genome segments from two or more genetically distinct oncolytic viruses wherein at least one parental virus is genetically engineered, comprises one or more chemically synthesized genomic segment, has been treated with chemical or physical mutagens, or is itself the result of a recombination event. Optionally, the methods include the use of the recombinant oncolytic virus that has undergone recombination in the presence of chemical mutagens, including but not limited to dimethyl sulfate and ethidium bromide, or physical mutagens, including but not limited to ultraviolet light and other forms of radiation.

Optionally, the methods include the use of oncolytic viruses with mutations including (insertions, substitutions, deletions or duplications) in one or more genome segments. Such mutations can comprise additional genetic information as a result of recombination with a host cell genome, or that comprise synthetic genes such as, for example, genes encoding agents that suppress anti-viral immune responses.

Optionally, the oncolytic virus is a mutant oncolytic virus. For example, the oncolytic virus may be modified by incorporation of mutated coat proteins, such as for example, into the virion outer capsid. The mutant oncolytic virus is, optionally, a mutant reovirus. Mutant reoviruses as described herein can contain a mutation that reduces or essentially eliminates expression of a sigma3 polypeptide or that results in the absence of a functional sigma3 polypeptide as described in U.S. Publication No. 2008/0292594, which is incorporated by reference herein in its entirety. Optionally, the mutant reoviruses used in the provided methods are mutated as described in U.S. Pat. No. 7,803, 385, which is incorporated by reference herein in its entirety.

A mutation as referred to herein can be a substitution, insertion or deletion of one or more nucleotides. Point mutations include, for example, single nucleotide transitions (purine to purine or pyrimidine to pyrimidine) or transversions (purine to pyrimidine or vice versa) and single- or multiple-nucleotide deletions or insertions. A mutation in a nucleic acid can result in one or more conservative or non-conservative amino acid substitutions in the encoded polypeptide, which may result in conformational changes or loss or partial loss of function, a shift in the reading frame of translation (frame-shift) resulting in an entirely different polypeptide encoded from that point on, a premature stop codon resulting in a truncated polypeptide (truncation), or a mutation in a virus nucleic acid may not change the encoded polypeptide at all (silent or nonsense). See, for example, Johnson and Overington, 1993, J. Mol. Biol. 233:716-38; Henikoff and Henikoff, 1992, Proc. Natl. Acad. Sci. USA 89:10915-19; and U.S. Pat. No. 4,554,101, for disclosure on conservative and non-conservative amino acid substitutions.

Mutations can be generated in the nucleic acid of an oncolytic virus using any number of methods known in the art. For example, site directed mutagenesis can be used to modify a reovirus nucleic acid sequence. One of the most common methods of site-directed mutagenesis is oligonucleotide-directed mutagenesis. In oligonucleotide-directed mutagenesis, an oligonucleotide encoding the desired change(s) in sequence is annealed to one strand of the DNA of interest and serves as a primer for initiation of DNA synthesis. In this manner, the oligonucleotide containing the sequence change is incorporated into the newly synthesized strand. See, for example, Kunkel, 1985, Proc. Natl. Acad. Sci. USA 82:488; Kunkel et al., 1987, Meth. Enzymol. 154:367; Lewis and Thompson, 1990, Nucl. Acids Res. 18:3439; Bohnsack, 1996, Meth. Mol. Biol. 57:1; Deng and Nickoloff, 1992, Anal. Biochem. 200:81; and Shimada, 1996, Meth. Mol. Biol. 57:157. Other methods are used routinely in the art to modify the sequence of a protein or polypeptide. For example, nucleic acids containing a mutation can be generated using PCR or chemical synthesis, or polypeptides having the desired change in amino acid sequence can be chemically synthesized. See, for example, Bang and Kent, 2005, Proc. Natl. Acad. Sci. USA 102: 5014-9 and references therein.

Also provided are compositions comprising the virus collected according to the methods provided herein and such compositions can include, for example, a pharmaceutically acceptable excipient. The herein provided compositions are administered in vitro or in vivo in a pharmaceutically acceptable carrier. A pharmaceutically acceptable carrier can be a solid, semi-solid, or liquid material that can act as a vehicle, carrier or medium for the reovirus. Thus, compositions containing an oncolytic virus and/or one or more of the provided agents can be in the form of tablets, pills, powders, lozenges, sachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Optionally, the compositions containing an oncolytic virus are suitable for infusion. For intravenous infusions, there are two types of fluids that are commonly used, crystalloids and colloids. Crystalloids are aqueous solutions of mineral salts or other water-soluble molecules. Colloids contain larger insoluble molecules, such as gelatin; blood itself is a colloid. The most commonly used crystalloid fluid is normal saline, a solution of sodium chloride at 0.9% concentration, which is close to the concentration in the blood (isotonic). Ringer's lactate or Ringer's acetate is another isotonic solution often used for large-volume fluid replacement. A solution of 5% dextrose in water, sometimes called D5W, is often used instead if the patient is at risk for having low blood sugar or high sodium.

Some examples of suitable carriers include phosphate-buffered saline or another physiologically acceptable buffer, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. A pharmaceutical composition additionally can include, without limitation, lubricating agents such as talc, magnesium stearate, and mineral oil; wetting agents; emulsifying and suspending agents; preserving agents such as methyl- and propylhydroxy-benzoates; sweetening agents; and flavoring agents. Pharmaceutical compositions can be formulated to provide quick, sustained or delayed release of a mutant reovirus after administration by employing procedures known in the art. In addition to the representative formulations described below, other suitable formulations for use in a pharmaceutical composition can be found in Remington: The Science and Practice of Pharmacy 22d edition Loyd V. Allen et al, editors, Pharmaceutical Press (2012). For preparing solid compositions such as tablets, a mutant reovirus can be mixed with a pharmaceutical carrier to form a solid composition. Optionally, tablets or pills can be coated or otherwise compounded to provide a dosage form affording the advantage of prolonged action. For example, a tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Liquid formulations that include a reovirus and/or agent for oral administration or for injection generally include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. These liquid or solid compositions may contain suitable pharmaceutically acceptable excipients as described herein. Such compositions can be administered by the oral or nasal respiratory route for local or systemic effect. Compositions in pharmaceutically acceptable solvents may be nebulized by use of inert gases. Nebulized solutions may be inhaled directly from the nebulizing device or the nebulizing device may be attached to a face mask tent or intermittent positive pressure breathing machine. Solution, suspension, or powder compositions may be administered, orally or nasally, from devices which deliver the formulation in an appropriate manner.

Another formulation that is optionally employed in the methods of the present disclosure includes transdermal delivery devices (e.g., patches). Such transdermal patches may be used to provide continuous or discontinuous infusion of the viruses and agents as described herein. The construction and use of transdermal patches for the delivery of pharmaceutical agents is well known in the art. See, for example, U.S. Pat. No. 5,023,252. Such patches can be constructed for continuous, pulsatile, or on-demand delivery of mutant reoviruses.

As described above, viruses and/or other agents can, if necessary, be coated in a liposome or micelle to reduce or prevent an immune response in a mammal that has developed immunity toward a virus or agent. Such compositions are referred to as immunoprotected viruses or agents. See, for example, U.S. Pat. Nos. 6,565,831 and 7,014,847.

In the provided methods, the oncolytic virus is administered, for example, systemically, in a manner so that it can ultimately contact the target tumor or tumor cells. The route by which the virus is administered, as well as the formulation, carrier or vehicle, depends on the location as well as the type of the target cells. A wide variety of administration routes can be employed. For example, for a solid tumor that is accessible, the virus can be administered by injection directly to the tumor. For a hematopoietic tumor, for example, the virus can be administered intravenously or intravascularly. For tumors that are not easily accessible within the body, such as metastases, the virus is administered in a manner such that it can be transported systemically through the body of the mammal and thereby reach the tumor (e.g., intravenously or intramuscularly). Alternatively, the virus can be administered directly to a single solid tumor, where it then is carried systemically through the body to metastases. The virus can also be administered subcutaneously, intraperitoneally, intrathecally or intraventricularly (e.g., for brain tumors), topically (e.g., for melanomas), orally (e.g., for oral or esophageal cancers), rectally (e.g., for colorectal cancers), vaginally (e.g., for cervical or vaginal cancers), nasally, by inhalation spray or by aerosol formulation (e.g., for lung cancers).

Optionally, the virus is administered continuously to a subject at least once per day or up to intermittently or continuously throughout the day on consecutive days, for a period of time for a first or subsequent round of treatment. Thus, the virus is administered, for example, to subjects by means of intravenous administration in any pharmacologically acceptable solution, or as an infusion over a period of time. For example, the substance may be administered systemically by injection (e.g., IM or subcutaneously) or taken orally daily at least once per day, or administered by infusion in a manner that results in the daily delivery into the tissue or blood stream of the subject. When the virus is administered by infusion over a period of time, the period of time is, for example, 1, 2, 3, 4, 5, 6, 7, 8, 9, 10, 12, or 24 hours, or any time between 1 and 24 hours, inclusive, or more. Optionally, the period of time is 5, 15, 30, 60, 90, 120, 150 or 180 minutes, or any time between 5 and 180 minutes, inclusive, or more. Thus, for example, the virus is administered by infusion for 60 minutes. Administrations can be repeated daily for 2, 3, 4, 5, 6, 7, 8, 9, 10, 14, 21, 28 days or any number of days between 2 and 28 days, inclusive, or longer.

The viruses as disclosed herein are administered in an amount that is sufficient (i.e., an effective amount) to effect the treatment of the cancer or proliferative disorder. A cancer or proliferative disorder is treated when administration of a treatment regimen including a virus to proliferating cells affects lysis (e.g., oncolysis) of the affected cells, resulting in a reduction in the number of abnormally, proliferating cells, a reduction in the size of a neoplasm, and/or a reduction in or elimination of symptoms (e.g., pain) associated with the proliferating disorder. As used herein, the term oncolysis means at least 10% of the proliferating cells are lysed (e.g., at least about 20%, at least about 30%, at least about 40%, at least about 50%, or at least about 75% of the cells are lysed). The percentage of lysis can be determined, for example, by measuring the reduction in the size of a neoplasm or in the number of proliferating cells in a mammal, or by measuring the amount of lysis of cells in vitro (e.g., from a biopsy of the proliferating cells). An effective amount of a virus used in a treatment regimen will be determined on an individual basis and may be based, at least in part, on the particular virus used; the individual's size, age, gender; and the size and other characteristics of the abnormally, proliferating cells. For example, for treatment of a human, approximately $10^3$ to $10^{12}$ plaque forming units (PFU) of a virus are used, depending on the type, size and number of proliferating cells or neoplasms present. The effective amount can be, for example, from about 1.0 PFU/kg body weight to about $10^{15}$ PFU/kg body weight (e.g., from about $10^2$ PFU/kg body weight to about $10^{13}$ PFU/kg body weight). Optionally, the effective amount is about $1\times10^8$ to about $1\times10^{12}$ PFU or TCID50. Optionally, the effective amount is about $3\times10^{10}$ to about $1\times10^{10}$ TCID50. By way of example, the effective amount can be between $3.0\times10^{10}$ to $4.5\times10^{10}$ TCID50. Optionally, the effective amount is $4.5\times10^{10}$ TCID50. Optionally, vials containing the viruses can include, for example, $5\times10^9$ to $1\times10^{11}$ TCID50/mL.

Optimal dosages of viruses and therapeutic agents, and compositions and kits comprising viruses and agents depend on a variety of factors. The exact amount required will vary from subject to subject, depending on the species, age, weight and general condition of the subject, the severity of the disease being treated, the particular virus and its mode of administration. Thus, it is not possible to specify an exact amount for every composition or kit. However, an appropriate amount can be determined by one of ordinary skill in the art using only routine experimentation given the guidance provided herein.

Effective dosages and schedules for administering the treatment regimens may be determined empirically. For example, animal models for a variety of proliferative disorders can be obtained from the Jackson Laboratory, 600 Main Street, Bar Harbor, Maine 04609 USA. Both direct (e.g., histology of tumors) and functional measurements (e.g., survival of a subject or size of a tumor) can be used to monitor response to therapies. These methods involve the sacrifice of representative animals to evaluate the population, increasing the animal numbers necessary for the experiments. Measurement of luciferase activity in the tumor provides an alternative method to evaluate tumor volume without animal sacrifice and allowing longitudinal population-based analysis of therapy. The dosage ranges for the administration of compositions are those large enough to produce the desired effect in which the symptoms of the disease are affected. The dosage should not be so large as to cause adverse side effects, such as unwanted cross-reactions and anaphylactic reactions. The dosage can be adjusted by the individual physician in the event of any counterindications.

Dosages vary and are administered in one or more dose administrations, for example, daily, for one or several days. The provided viruses and therapeutic agents are administered in a single dose or in multiple doses (e.g., two, three, four, six, or more doses). For example, where the administration is by infusion, the infusion can be a single sustained dose or can be delivered by multiple infusions. Treatment may last from several days to several months or until diminution of the disease is achieved.

The provided methods may be further combined with other tumor therapies such as chemotherapy, radiotherapy, surgery, hormone therapy and/or other immunotherapies. Suitable additional therapeutic agents include, but are not limited to, analgesics, anesthetics, analeptics, corticosteroids, anticholinergic agents, anticholinesterases, anticonvulsants, antineoplastic agents, allosteric inhibitors, anabolic steroids, antirheumatic agents, psychotherapeutic agents, neural blocking agents, anti-inflammatory agents, antihelmintics, antibiotics, anticoagulants, antifungals, antihistamines, antimuscarinic agents, antimycobacterial agents, antiprotozoal agents, antiviral agents, dopaminergics, hematological agents, immunological agents, muscarinics, protease inhibitors, vitamins, growth factors, and hormones. The choice of agent and dosage can be determined readily by one of skill in the art based on the given disease being treated.

Combinations of the provided viruses and therapeutic agents are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents.

When one compound is administered prior to another compound, the first compound is administered minutes, hours, days, or weeks prior to administration of the second compound. For example, the first compound can be administered at 1, 2, 3, 4, 5, 6, 7, 8, 9, 10, 12, 24, 36, 48, 60, or 72 hours, or any time between 1 and 72 hours, inclusive, prior to administration of a second compound. Optionally, the first compound is administered more than 72 hours prior to the second compound. By way of another example, the first compound can be administered at 1, 5, 15, 30, 60, 90, 120, 150 or 180 minutes, or any time between 1 and 180 minutes, inclusive, prior to administration of a second compound. Optionally, the first compound is administered at 1, 2, 3, 4, 5, 6, 7, 14, 21, or 28 days, or at any timepoint between 1 and 28, inclusive, days prior to administration of the second compound. Optionally, the first compound is administered more than 28 days prior to the second compound.

Oncolytic viruses or a pharmaceutical composition comprising such viruses can be packaged into a kit. The kit also includes one or more additional agents or pharmaceutical compositions comprising the additional agents. The kit can include chemotherapeutic agents or cancer immunotherapeutic agents. Optionally, the kit includes an immune checkpoint inhibitor.

The oncolytic viruses and/or additional agents and pharmaceutical compositions containing the same can be packaged in one or more containers. When the kits contain pharmaceutical compositions, the pharmaceutical compositions can be formulated in a unit dosage form. The term "unit dosage forms" refers to physically discrete units suitable as unitary dosages for human subjects and other mammals, each unit containing a predetermined quantity of an oncolytic virus or other agent, e.g., immune checkpoint inhibitor calculated to produce the desired therapeutic effect in association with a suitable pharmaceutically acceptable carrier. Optionally, the kit includes a reovirus and an immune checkpoint inhibitor.

The oncolytic virus in the provided kits can be any of the oncolytic viruses described herein. The provided kits can include more than one dose of the oncolytic virus. Optionally, each dose of oncolytic virus comprises approximately $10^3$ to $10^{12}$ plaque forming units (PFU) of the oncolytic virus. Optionally, each dose comprises approximately $10^8$ to $10^{12}$ PFU of the oncolytic virus. Optionally, each dose comprises approximately $10^8$ to $10^{12}$ TCID50 of the oncolytic virus. Optionally, each dose comprises approximately $1\times10^{10}$ to $3\times10^{10}$ TCID50 of the oncolytic virus. By way of example, each dose can be between $3.0\times10^{10}$ to $4.5\times10^{10}$ TCID50. Optionally, each dose is $4.5\times10^{10}$ TCID50. Optionally, vials containing the viruses can include, for example, $5\times10^9$ to $1\times10^{11}$ TCID50/mL.

As used herein the terms treatment, treat, treating or ameliorating refers to a method of reducing the effects of a disease or condition or symptom of the disease or condition. Thus, in the disclosed method, treatment can refer to a 10% or greater, 20% or greater, 30% or greater, 40% or greater, 50% or greater, 60% or greater, 70% or greater, 80% or greater, 90% or greater or 100% reduction or amelioration in the severity of an established disease or condition or symptom of the disease or condition. For example, the method for treating cancer is considered to be a treatment if there is a 10% or greater reduction in one or more symptoms of the disease in a subject as compared to control. Thus, the reduction can be 10% or greater, 20% or greater, 30% or greater, 40% or greater, 50% or greater, 60% or greater, 70% or greater, 80% or greater, 90% or greater, 100% or any percent reduction in the range of 10% to 100% as compared to native or control levels. It is understood that treatment does not necessarily refer to a cure or complete ablation of the disease, condition or symptoms of the disease or condition.

As used herein, the term subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The term does not denote a particular age or sex. Thus, adult and newborn subjects, whether male or female, are intended to be covered. As used herein, the terms patient and subject may be used interchangeably and can refer to a subject with a disease or disorder. The term patient or subject includes human and veterinary subjects.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if an inhibitor is disclosed and discussed and a number of modifications that can be made to a number of molecules including the inhibitor are discussed, each and every combination and permutation of the inhibitor, and the modifications that are possible are specifically contemplated unless specifically indicated to the contrary. Likewise, any subset or combination of these is also specifically contemplated and disclosed. This concept applies to all aspects of this disclosure including, but not limited to, steps in methods of using the disclosed compositions. Thus, if there are a variety of additional steps that can be performed it is understood that each of these additional steps can be performed with any specific method steps or combination of method steps of the disclosed methods, and that each such combination or subset of combinations is specifically contemplated and should be considered disclosed.

Throughout this application, various publications are referenced. The disclosures of these publications in their entireties are hereby incorporated by reference into this application.

A number of aspects have been described. Nevertheless, it will be understood that various modifications may be made. Furthermore, when one characteristic or step is described, it can be combined with any other characteristic or step herein even if the combination is not explicitly stated. Accordingly, other aspects are within the scope of the claims.

EXAMPLES

Example 1. Lysis, Extraction and Purification of Reovirus from Host Cells

1% Triton™ X-100 is used in the current validated reovirus manufacturing process to lyse HEK293 cells, to maximize viral particle recovery at the upstream harvest step. However, Triton™ X-100 was added to the REACH list and cannot be used for commercial production in the European Union due to its environmental impact. Therefore, an alternative detergent needs to be identified and tested to avoid any delays in reovirus manufacture.

Table 1 is a list of alternatives tested in this example.

TABLE 1

| Detergent | Type | Grade Available/ Quality Level | REACH Status |
|---|---|---|---|
| Deviron ® 16 | Zwitterionic | Quality Level 400 | Low risk |
| ECOSURF ™-EH9 | Non-ionic | Quality Level 200 | Low risk |
| Octyl β-D-Glucopyranoside (OGP) | Non-ionic | Quality Level 300 | Low risk |
| Sodium Deoxycholate (NaDOC) | Anionic | Quality Level 400 | Low risk |
| Tween ® 20 | Non-ionic | USP, Multi-compendial | Low risk |
| Tween ® 80 | Non-ionic | USP, Multi-compendial | Low risk |
| Tergitol 15-S-9 | Non-ionic | Quality Level 200 | Low risk |

Alternative candidate detergents were assessed at varying concentrations (0.50, 10, 20) and durations (1 hour, 2 hours, 3 hours) during the lysis step, followed by incubation with Benzonase® to digest host cell DNA (HC DNA). The detergents tested were Deviron C6; ECOSURF EH-9; Octyl β-D-Glucopyranoside (OGP); Sodium Deoxycholate (Na-DOC); Tween® 20; Tween® 80, and Tergitol 15-S-9. Samples were analyzed for virus particle recovery (HPLC), infectious viral particles (TCID5), and residual HC DNA. These data were compared to Triton™ X-100 and cells lysed via freeze/thaw cycles as controls. The results are shown in Tables 2 and 3.

TABLE 2

| Conditions | HPLC Titer (vp/mL) | Detergent Efficiency vs Triton ™ X-100 (%) |
|---|---|---|
| Supernatant CTL - centrifuged 3 dpi cell culture | $4.66 \times 10^{11}$ | |
| Triton ™ X-100 0.91% CTL, 1 hr incubation | $4.67 \times 10^{11}$ | 100 |
| ECOSURF- ES-9 0.5%, 1 hr incubation | $3.02 \times 10^{11}$ | 64.7 |
| ECOSURF- ES-9 1.0%, 1 hr incubation | $3.09 \times 10^{11}$ | 66.2 |
| ECOSURF- ES-9 2.0%, 1 hr incubation | $2.14 \times 10^{11}$ | 45.8 |
| ECOSURF- ES-9 0.5%, 2 hr incubation | No reovirus peak | 0 |
| ECOSURF- ES-9 1.0%, 2 hr incubation | No reovirus peak | 0 |
| ECOSURF- ES-9 2.0%, 2 hr incubation | No reovirus peak | 0 |
| ECOSURF- ES-9 0.5%, 3 hr incubation | No reovirus peak | 0 |
| ECOSURF- ES-9 1.0%, 3 hr incubation | No reovirus peak | 0 |
| ECOSURF- ES-9 2.0%, 3 hr incubation | No reovirus peak | 0 |
| Tergitol 15-S-9 0.5%, 1 hr incubation | $3.12 \times 10^{11}$ | 66.8 |
| Tergitol 15-S-9 1.0%, 1 hr incubation | $2.48 \times 10^{11}$ | 53.1 |
| Tergitol 15-S-9 2.0%, 1 hr incubation | $3.15 \times 10^{11}$ | 67.5 |
| Tergitol 15-S-9 0.5%, 2 hr incubation | $4.19 \times 10^{11}$ | 89.7 |
| Tergitol 15-S-9 1.0%, 2 hr incubation | $4.55 \times 10^{11}$ | 97.4 |
| Tergitol 15-S-9 2.0%, 2 hr incubation | $4.33 \times 10^{11}$ | 92.7 |

TABLE 2-continued

| Alternative Detergents - Viral Titer Results (HPLC) | | |
| --- | --- | --- |
| Conditions | HPLC Titer (vp/mL) | Detergent Efficiency vs Triton ™ X-100 (%) |
| Tergitol 15-S-9 0.5%, 3 hr incubation | $3.59 \times 10^{11}$ | 76.9 |
| Tergitol 15-S-9 1.0%, 3 hr incubation | $3.61 \times 10^{11}$ | 77.3 |
| Tergitol 15-S-9 2.0%, 3 hr incubation | $3.90 \times 10^{11}$ | 83.5 | dpi: days post infection;
CTL: control;
hr: hour;
vp: viral particle

TABLE 3

| Alternative Detergents - Viral Titer Results (HPLC) | | |
| --- | --- | --- |
| Conditions | HPLC Titer (vp/mL) | Detergent Efficiency vs Triton ™ X-100 (%) |
| Supernatant CTL - centrifuged 3 dpi cell culture | $3.18 \times 10^{11}$ | |
| Triton ™ X-100 0.91% CTL, 1 hr incubation | $3.62 \times 10^{11}$ | 100 |
| Octyl ß-D-Glucopyranoside 0.5%, 1 hr incubation | $3.40 \times 10^{11}$ | 93.9 |
| Octyl ß-D-Glucopyranoside 1.0%, 1 hr incubation | $2.82 \times 10^{11}$ | 77.9 |
| Octyl ß-D-Glucopyranoside 1.5%, 1 hr incubation | $1.86 \times 10^{11}$ | 51.4 |
| Deviron C16 0.1%, 1 hr incubation | $2.67 \times 10^{11}$ | 73.8 |
| Deviron C16 0.25%, 1 hr incubation | $2.02 \times 10^{11}$ | 55.8 |
| Deviron C16 0.5%, 1 hr incubation | $9.20 \times 10^{10}$ | 25.4 |
| Sodium deoxycholate 0.1%, 1 hr incubation | $4.19 \times 10^{11}$ | 115.8 |
| Sodium deoxycholate 0.25%, 1 hr incubation | $3.12 \times 10^{11}$ | 86.2 |
| Sodium deoxycholate 0.5%, 1 hr incubation | No reovirus peak | N/A | dpi: days post infection;
CTL: control;
hr: hour;
vp: viral particle

Conditions resulting in viral particle recoveries >80% versus the Triton™ X-100 control were selected for full downstream analysis. Viral recoveries ranging from 90-98% resulted from 0.50% Octyl β-D-Glucopyranoside (OGP) and 2 hr Tergitol 15-S-9 (at 0.50%, 10%, 2%) conditions. Sodium Deoxycholate (NaDOC) at 0.10% showed the best efficiency, 160% higher than the Triton™ X-100. However, there is a trend where increasing NaDOC concentrations results in decreasing viral titer with no detectable viral particles for the 0.50% NaDOC concentration. Also, because NaDOC is an anionic detergent, it is not compatible with the ion exchange purification step, unless it is first removed from the sample before purification using the ion exchange column. Therefore, it was decided not to continue with this detergent. As noted for NaDOC above, OGP and Deviron C-16 also show decreasing titer with increasing detergent concentrations, suggesting these higher detergent amounts may degrade reovirus.

Tween® 20 was tested at varying concentrations (0.5%, 10%, 1.5%) and incubation times (1 hr, 2 hr, 3 hr). The results are shown in Table 4.

TABLE 4

| Tween ® 20 Viral Titer Results (HPLC) | | |
| --- | --- | --- |
| Conditions | HPLC Titer (vp/mL) | Detergent Efficiency vs Triton ™ X-100 (%) |
| Supernatant CTL - centrifuged 3 dpi cell culture | $4.66 \times 10^{11}$ | |
| Triton ™ X-100 0.91% CTL, 1 hr incubation | $4.67 \times 10^{11}$ | 100 |
| Tween ® 20 0.5%, 1 hr incubation | $2.77 \times 10^{11}$ | 59.3 |
| Tween ® 20 1.0%, 1 hr incubation | $2.82 \times 10^{11}$ | 60.4 |
| Tween ® 20 1.5%, 1 hr incubation | $3.04 \times 10^{11}$ | 65.1 |
| Tween ® 20 0.5%, 2 hr incubation | $3.03 \times 10^{11}$ | 64.9 |
| Tween ® 20 1.0%, 2 hr incubation | $2.76 \times 10^{11}$ | 59.1 |
| Tween ® 20 1.5%, 2 hr incubation | $2.74 \times 10^{11}$ | 58.7 |
| Tween ® 20 0.5%, 3 hr incubation | $2.87 \times 10^{11}$ | 61.4 |

TABLE 4-continued

| | | Detergent Efficiency vs Triton ™ X-100 (%) |
|---|---|---|
| Conditions | HPLC Titer (vp/mL) | |
| Tween ® 20 1.0%, 3 hr incubation | $2.81 \times 10^{11}$ | 60.2 |
| Tween ® 20 1.5%, 3 hr incubation | $2.78 \times 10^{11}$ | 59.5 | dpi: days post infection;

CTL: control;

hr: hour;

vp: viral particle

None of these conditions resulted in viral particle recoveries >80 versus Triton™ X-100, therefore, further optimization of the Tween® 20 lysis conditions was required. These results are shown in Table 5.

TABLE 5

Tween ® 20 Viral Titer Results (HPLC).

| Conditions | HPLC Titer (vp/mL) | Detergent Efficiency vs Triton ™ X-100 (%) |
|---|---|---|
| Supernatant CTL - centrifuged 3 dpi cell culture | $3.18 \times 10^{11}$ | |
| Triton ™ X-100 0.91% CTL | $3.62 \times 10^{11}$ | 100 |
| Tween ® 20 0.5% - Tris 50 mM pH 7, 1 hr incubation | $2.71 \times 10^{11}$ | 74.9 |
| Tween ® 20 0.5% - Tris 50 mM pH 7.5, 1 hr incubation | $2.68 \times 10^{11}$ | 74.0 |
| Tween ® 20 0.5% - Tris 50 mM pH 8, 1 hr incubation | $2.74 \times 10^{11}$ | 75.7 |
| Tween ® 20 0.5% - PO4 10 mM pH 7, 1 hr incubation | $2.62 \times 10^{11}$ | 72.4 |
| Tween ® 20 0.5% - PO4 10 mM pH 7.5, 1 hr incubation | $2.58 \times 10^{11}$ | 71.3 |
| Tween ® 20 0.5% - PO4 10 mM pH 8, 1 hr incubation | $2.57 \times 10^{11}$ | 71.0 |
| Tween ® 20 0.5% - PO4 20 mM pH 7, 1 hr incubation | $2.62 \times 10^{11}$ | 72.4 |
| Tween ® 20 0.5% - PO4 20 mM pH 7.5, 1 hr incubation | $2.71 \times 10^{11}$ | 74.9 |
| Tween ® 20 0.5% - PO4 20 mM pH 8, 1 hr incubation | $2.72 \times 10^{11}$ | 75.1 |
| Tween ® 20 1% - Tris 50 mM pH 7, 1 hr incubation | $2.47 \times 10^{11}$ | 68.2 |
| Tween ® 20 1% - Tris 50 mM pH 7.5, 1 hr incubation | $2.40 \times 10^{11}$ | 66.3 |
| Tween ® 20 1% - Tris 50 mM pH 8, 1 hr incubation | $2.43 \times 10^{11}$ | 67.1 |
| Tween ® 20 1% - PO4 10 mM pH 7, 1 hr incubation | $2.36 \times 10^{11}$ | 65.2 |
| Tween ® 20 1% - PO4 10 mM pH 7.5, 1 hr incubation | $2.42 \times 10^{11}$ | 66.9 |
| Tween ® 20 1% - PO4 10 mM pH 8, 1 hr incubation | $2.38 \times 10^{11}$ | 65.7 |
| Tween ® 20 1% - PO4 20 mM pH 7, 1 hr incubation | $2.40 \times 10^{11}$ | 66.3 |
| Tween ® 20 1% - PO4 20 mM pH 7.5, 1 hr incubation | $2.76 \times 10^{11}$ | 76.2 |
| Tween ® 20 1% - PO4 20 mM pH 8, 1 hr incubation | $2.94 \times 10^{11}$ | 81.2 | dpi: days post infection;

CTL: control;

hr: hour;

PO4: Sodium Phosphate;

vp: viral particle

There is a positive trend for the 20 mM sodium phosphate (PO4) buffer lysis condition with increasing pH. The 1% Tween® 20 results are better than the 0.5% Tween® 20 results for the same pH conditions. The 1% Tween® 20 with 20 mM sodium phosphate at pH 8 shows a titer above the cut-off value of 80% of Triton™ X-100. However, the Tween® 20 lysis conditions vs Triton™ X-100 were not improved using 10 mM sodium phosphate buffer, or 50 mM Tris buffer at pH 7.0, 7.5, or 8.0.

The results of further optimization of the 1% Tween® 20 lysis conditions are shown in Table 6.

TABLE 6

| Further Optimization of Tween ® 20 - Viral Titer Results (HPLC). | | |
|---|---|---|
| Conditions | HPLC Titer (vp/mL) | Detergent Efficiency vs Triton ™ X-100 (%) |
| Supernatant CTL - centrifuged 3 dpi cell culture | $3.18 \times 10^{11}$ | |
| Triton ™ X-100 0.91% CTL | $3.28 \times 10^{11}$ | 100 |
| Tween ® 20 1%, 2 hr, salt −80° C. | $3.32 \times 10^{11}$ | 101 |
| Tween ® 20 1%, 2 hr, salt O/N 4° C.-80° C. | $2.92 \times 10^{11}$ | 88 |
| Tween ® 20 1%, 2 hr −80° C. | $3.24 \times 10^{11}$ | 99 |
| Tween ® 20 1%, 2 hr O/N 4° C.-80° C. | $2.77 \times 10^{11}$ | 83 |
| Tween ® 20 1%, 3 hr, salt −80° C. | $2.85 \times 10^{11}$ | 87 |
| Tween ® 20 1%, 3 hr, salt O/N 4° C.-80° C. | $2.81 \times 10^{11}$ | 85 |
| Tween ® 20 1%, 3 hr −80° C. | $3.21 \times 10^{11}$ | 98 |
| Tween ® 20 1%, 3 hr O/N 4° C.-80° C. | $2.86 \times 10^{11}$ | 86 |
| Tween ® 20 1%, 4 hr, salt −80° C. | $2.84 \times 10^{11}$ | 87 |
| Tween ® 20 1%, 4 hr, salt O/N 4° C.-80° C. | $2.85 \times 10^{11}$ | 86 |
| Tween ® 80 1%, 1 hr −80° C. | $3.03 \times 10^{11}$ | 92 |
| Tween ® 80 1%, 1 hr O/N 4° C.-80° C. | $2.79 \times 10^{11}$ | 84 |
| Tween ® 80 1%, 2 hr, salt −80° C. | $3.12 \times 10^{11}$ | 95 |
| Tween ® 80 1%, 2 hr, salt O/N 4° C.-80° C. | $2.59 \times 10^{11}$ | 78 |
| Tween ® 80 1.5%, 1 hr −80° C. | $2.84 \times 10^{11}$ | 87 |
| Tween ® 80 1.5%, 1 hr O/N 4° C.-80° C. | $2.77 \times 10^{11}$ | 83 |
| Tween ® 80 1.5%, 2 hr, salt −80° C. | $3.09 \times 10^{11}$ | 94 |
| Tween ® 80 1.5%, 2 hr, salt O/N 4° C.-80° C. | $2.82 \times 10^{11}$ | 85 | dpi: days post infection;
CTL: control;
hr: hour;
O/N: overnight;
vp: viral particle Salt in Table 6 refers to 200 mM NaCl, which was included to see if it would improve the Tween® 20 lysis conditions.

Further optimization of the 1% Tween® 20, 20 mM phosphate lysis buffer, pH 8 included longer detergent incubation times (1 hr, 2 hr, 3 hr) and the addition of 200 mM NaCl post-Benzonase® digestion. For both Tween® detergents (Tween® 20 and Tween® 80), the addition of 200 mM NaCl did not improve viral particle recovery. Incubation for 2 hours with Tween® 20 resulted in the highest PLC recoveries. Lysis with Tween® 80 resulted in HPLC recoveries >80 vs. Triton™ X-100. However, as the Tween® 80 results are comparable to Tween® 20, it was decided to move forward with Tween® 20.

Further analysis of alternative detergents for the replacement of Triton™ X-100, including infectious viral titers, are shown in Table 7. Note that although the Triton™ X-100 control appears to have higher HPLC and TCID50 recoveries than Tween® 20, at the larger manufacturing scale (1.25 L), this trend is reversed, with Tween® 20 resulting in improved HPLC and TCID50 titers versus Triton™ X-100.

TABLE 7

| Triton ™ X-100 Replacement-Detergent Viral Titer (TCID50) Results | | |
|---|---|---|
| Conditions | TCID50 Titer (TCID50/mL) | Detergent Efficiency vs Triton ™ X-100 (%) |
| Supernatant CTL - centrifuged 3 dpi cell culture | $8.46 \times 10^{09}$ | |
| Triton ™ X-100 0.91% CTL | $1.63 \times 10^{10}$ | 100 |
| Tween ® 20 1% - PO4 20 mM pH 7 | $9.81 \times 10^{09}$ | 60.1 |
| Tween ® 20 1% - PO4 20 mM pH 7.5 | $9.76 \times 10^{09}$ | 59.8 |
| Tween ® 20 1% - PO4 20 mM pH 8 | $1.48 \times 10^{10}$ | 90.7 |
| Octyl ß-D-Glucopyranoside 0.5% | $1.64 \times 10^{10}$ | 100.3 |
| Octyl ß-D-Glucopyranoside 1.0% | $7.68 \times 10^{09}$ | 47.1 |
| Octyl ß-D-Glucopyranoside 1.0% 4° C. O/N | $3.00 \times 10^{10}$ | Invalid assay result |
| Deviron C16 0.1% | $4.27 \times 10^{09}$ | 26.2 |
| Deviron C16 0.25% | $5.00 \times 10^{08}$ | 3.1 |
| Deviron C16 0.25% 4° C. O/N | $1.30 \times 10^{09}$ | 8.0 |
| Sodium deoxycholate 0.1% | $2.10 \times 10^{10}$ | 128.9 |
| Sodium deoxycholate 0.25% | $1.58 \times 10^{10}$ | 96.7 |
| Sodium deoxycholate 0.25% 4° C. O/N | $1.76 \times 10^{10}$ | 107.6 | dpi: days post infection;
CTL: control;
PO4: Sodium Phosphate;
O/N: overnight incubation at 4° C.

The TCID50 viral titer results show a similar trend to the HPLC data. Detergents resulting in the best recovery of infectious viral titer versus Triton™ X-100 were 1% Tergitol 15-S-9, 1% Tween® 20 in 20 mM PO4 buffer pH 8, 0.5% OGP, and 0.1% NaDOC.

In summary, the screening of different alternative detergents identified a few potential candidates (OGP, NaDOC, Tween® 20, Tergitol 15-S-9) to replace the Triton™ X-100.

Three conditions were used to assess the detergents' impact on the manufacturing process at the 1.25 L scale versus the current Triton™ X-100 process (Table 8). The following detergents and conditions were tested: 1% Tween® 20 with 20 mM NaPO$_4$ lysis buffer pH 8.0, 2 hr incubation; 1% Tergitol 15-S-9 for 1 hr incubation; and 0.5% OGP for 1 hr incubation. For Tergitol 15-S-9, the total HPLC recovery was 21% greater than Triton™ X-100 ($5.28 \times 10^{13}$ vs $4.35 \times 10^{13}$), and the total infectious viral particles (TCID50) was 25% higher than Triton™ X-100 ($3.22 \times 10^{12}$ vs $2.57 \times 10^{12}$). For 0.5% OGP, the total viral particle yield was $8.24 \times 10^{13}$ HPLC and total infectious viral particle yield was $2.10 \times 10^{12}$ TCID50. For both total viral particle yield (HPLC) and infectious viral particle yield (TCID50), the Tween® 20 results are better than the Triton™ X-100. Tween® 20 resulted in 54% and 29% higher yield than Triton™ X-100 for total HPLC ($1.53 \times 10^{14}$ HPLC vs $9.94 \times 10^{13}$ HPLC) and TCID50 ($3.27 \times 10^{12}$ vs $2.53 \times 10^{12}$), respectively. These are the best yields of the 3 detergents tested in the reovirus production method at the 1.25 L scale.

TABLE 8

Summary of Bulk Purified Material Using 3 Different Detergents (1.25 L Manufacturing Scale)

| Detergent Conditions | Viral Particles (HPLC) | | Infectious Viral Particles (TCID50) | | Host Cell Protein (HCP) | | Host Cell DNA (HC DNA) | |
|---|---|---|---|---|---|---|---|---|
| | vp/mL | Total vp | TCID50/mL | Total TCID50 | ng/mL | µg | ng/mL | µg |
| 1% Tergitol 15-S-9, 1 hr | $9.62 \times 10^{11}$ | $5.28 \times 10^{13}$ | $5.87 \times 10^{10}$ | $3.22 \times 10^{12}$ | <7 | <0.38 | 68.7 | 3.77 |
| 1% Triton™ X-100, 1 hr | $7.82 \times 10^{11}$ | $4.35 \times 10^{13}$ | $4.62 \times 10^{10}$ | $2.57 \times 10^{12}$ | 17.8 | 0.99 | 88.3 | 4.91 |
| 0.5% OGP, 1 hr | $1.56 \times 10^{12}$ | $8.24 \times 10^{13}$ | $3.98 \times 10^{10}$ | $2.10 \times 10^{12}$ | 154 | 8.1 | <20 | <1.06 |
| 1% Tween ® 20, 20 mM PO4 pH 8.0, 2 hr | $2.58 \times 10^{12}$ | $1.53 \times 10^{14}$ | $5.51 \times 10^{10}$ | $3.27 \times 10^{12}$ | 35 | 2.1 | 163.2 | 9.69 |
| 1% Triton ™ X-100, 1 hr | $1.89 \times 10^{12}$ | $9.94 \times 10^{13}$ | $4.81 \times 10^{10}$ | $2.53 \times 10^{12}$ | 15.3 | 0.8 | 94.9 | 5.00 | hr: hour vp: viral particle

From Table 8, the data suggests that cell lysis using Tween® 20 may show lower efficiency at reducing HC DNA and host cell protein (HCP). Additional small-scale experiments were performed as per Table 9 below to determine the optimal Benzonase® digestion conditions to ensure Tween® 20 produces HC DNA and HCP levels similar or lower than those resulting from the Triton™ X-100 process.

TABLE 9

Benzonase ® Optimization Following Cell Lysis with 1% Tween ® 20, 20 mM Na$_2$HPO$_4$, pH 8.0, 2 hr Incubation

| Detergent Conditions | Concentration (v/v) | Incubation (37° C., 120 rpm) | Benzonase ® Digestion Conditions |
|---|---|---|---|
| Triton ™ X-100 (Control) | 1% | 1 hour | 60 minutes, 10 U/mL |
| Tween ® 20 (QL300) in 20 mM Sodium Phosphate, pH 8 | 1% | 2 hours | 60 minutes, 10 U/mL |

TABLE 9-continued

Benzonase ® Optimization Following Cell Lysis with 1% Tween ® 20, 20 mM Na$_2$HPO$_4$, pH 8.0, 2 hr Incubation

| Detergent Conditions | Concentration (v/v) | Incubation (37° C., 120 rpm) | Benzonase ® Digestion Conditions |
|---|---|---|---|
| Tween ® 20 (QL500) in 20 mM Sodium Phosphate, pH 8 | 1% | 2 hours | 60, 90, 120, 180, 240 minutes, 20 U/mL | hr: hour

Figure 2:
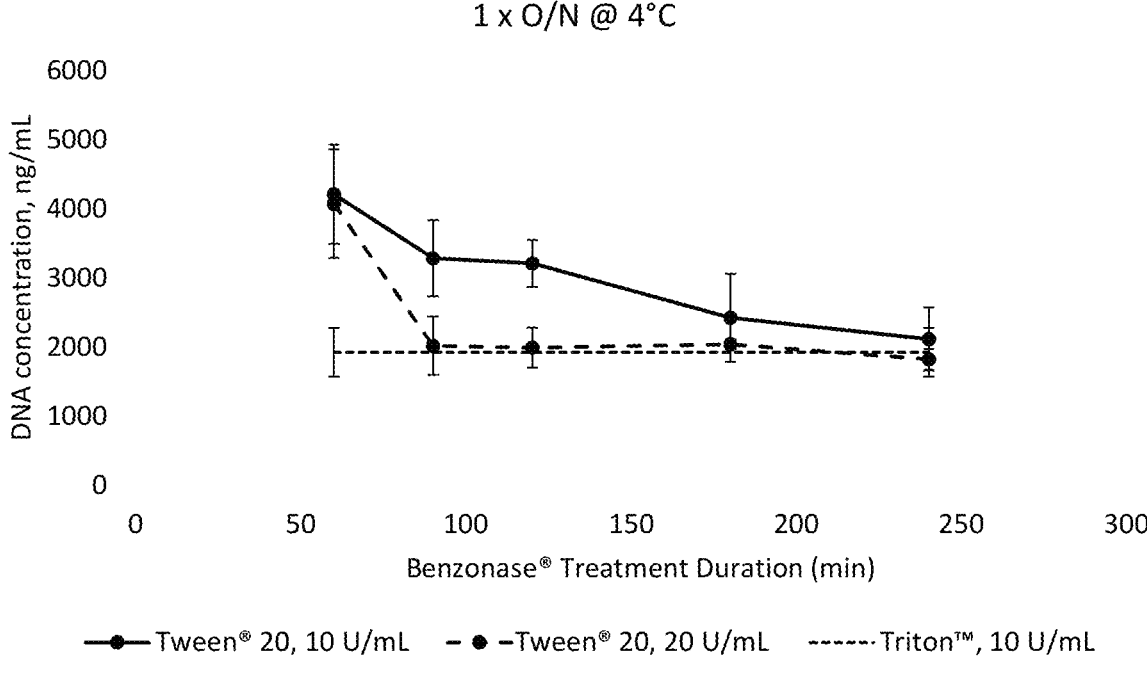
FIG. 2 is a graph showing residual HC DNA results of the same testing materials as in FIG. 1, after one overnight (O/N) storage at 2-8° C. post-clarification.
Figure 3:
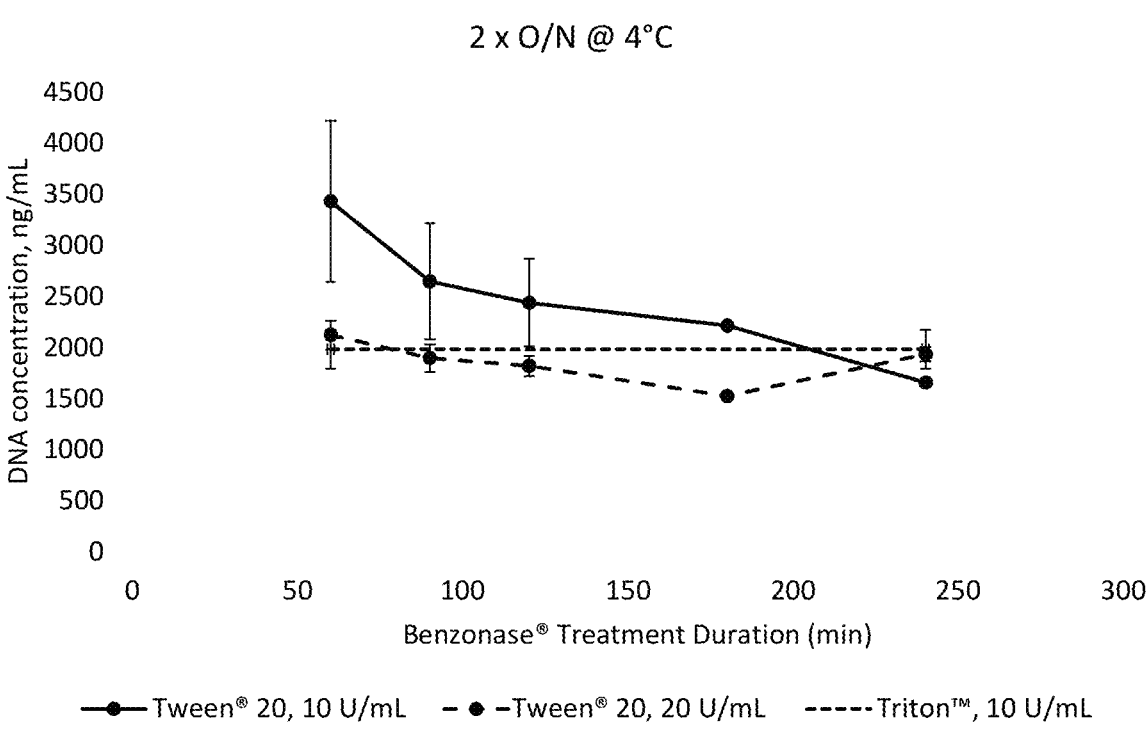
FIG. 3 is a graph showing residual HC DNA results of the same testing materials as in FIG. 1, after two overnight storages at 2-8° C. post-clarification.
Figure 4:
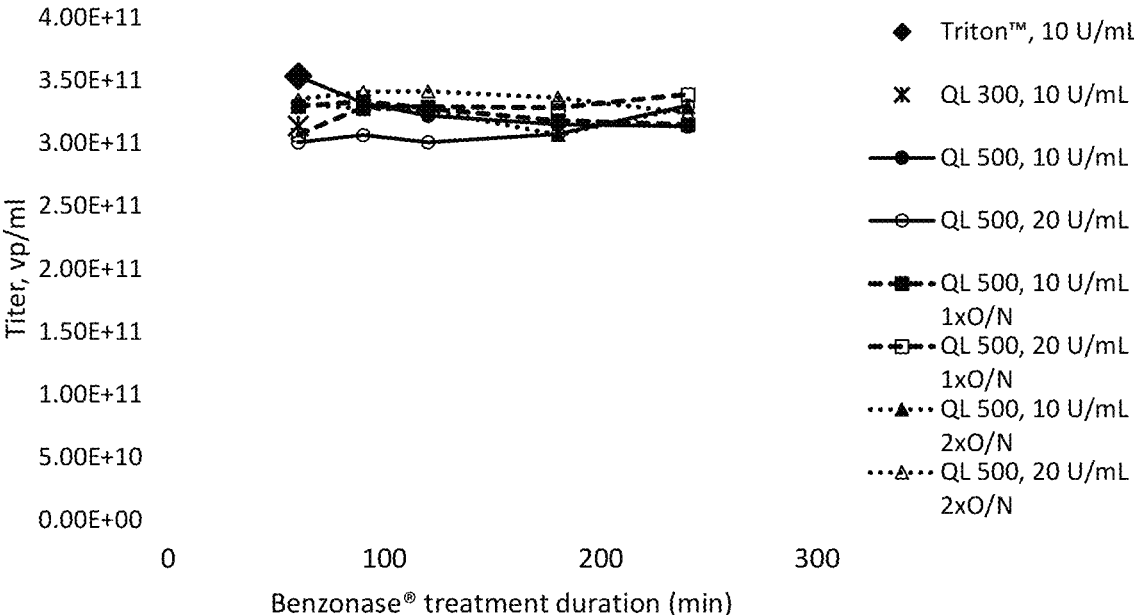
FIG. 4 is a graph showing total viral particle titer results for the same testing materials as in FIG. 1 (post-clarification; solid lines), as in FIG. 2 (1×O/N storage at 2-8° C. post-clarification; dashed lines), and as in FIG. 3 (2×O/N storage at 2-8° C. post-clarification; dotted lines). Results of testing material lysed with 1% Triton™ X-100 for 1 hour incubation and testing material lysed using 1% of QL300 grade Tween® 20 in 20 mM Na$_2$HPO$_4$ pH 8.0 lysis buffer for 2 hour incubation, both treated with 10 U/mL of Benzonase® for 60 minutes are included as controls. Increasing Benzonase® concentration from 10 to 20 U/mL or changing Benzonase® treatment duration from 60 to 240 minutes did not negatively impact the total reovirus titer (HPLC), for up to 2 days of overnight storage at 2-8° C. before freezing at −80° C. QL: Quality Level.

As shown in Table 9 and FIGS. 1-3, increasing Benzonase® concentration from 10 to 20 U/mL lowered the residual HC DNA levels to those obtained with the Triton™ X-100 cell lysis. Optimal Benzonase® digestion duration, when used at a 20 U/mL concentration, ranges from 90-240 minutes.

As shown in Table 9 and FIGS. 1-4, increasing Benzonase® concentration from 10 to 20 U/mL or changing Benzonase® treatment duration from 60 to 240 minutes did not negatively impact the total reovirus titer (HPLC), for up to 2 days of overnight storage at 2-8° C. post-clarification.

Figure 5:
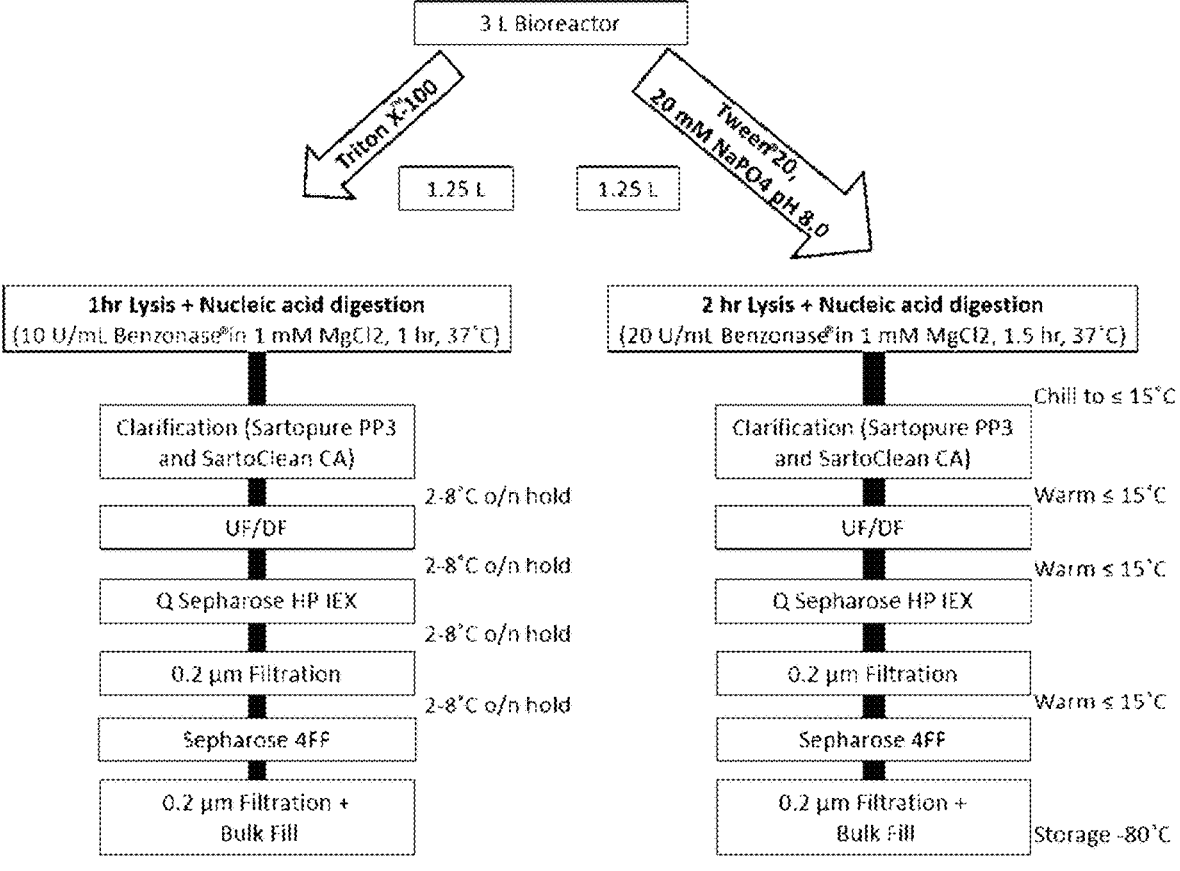
FIG. 5 is a schematic showing the extraction and purification protocol using Triton™ X-100 (left side) and the extraction and purification protocol described in the present application (right side).

In summary, cell lysis with 1% Tween® 20 in 20 mM NaPO4, pH 8.0 lysis buffer for 2 hr incubation, followed by Benzonase® digestion for 1.5 hr at 20 U/mL can be used as shown in the examples and described throughout the application. FIG. 5 shows a schematic of the reovirus purification workflow, including the virus extraction protocol.

The following is an overall summary of the production and extraction of virus as described in the examples. HEK293S cells were thawed and expanded for approximately 6-8 passages until an adequate quantity of cells required to seed the bioreactor at 1.5 L at a target Viable Cell Density of $0.4 \times 10^6$ cells/mL was reached. The bioreactor operating conditions are Temperature=37° C.; Dissolved oxygen=40% air saturation; pH=7.2±0.05; and Agitation rate=150 rpm final (ramp). Once the cell density was reached (between $1.8-2.4 \times 10^6$ cells/mL), the culture is infected. A viral stock was prepared in 24 mL medium for a Multiplicity of Infection (MOI) of 0.5 virus/cell. The virus was added in about 1.5 L of fresh medium to bring the final volume to 3 L. Cell viability was monitored, and cells were harvested either 3 days post-infection (if the viability is below 35%) or at 4 days post-infection. Glucose was added as needed at time of infection.

For harvest, the culture volume of the bioreactor was split into 2 equal volumes that were each distributed in 2×3.5 L Chemap bioreactor vessels. The Triton™ X-100, 0.91% v/v final was added to one vessel and Tween® 20, 1% final in a 20 mM NaPO$_4$ lysis buffer at pH 8.0 was added to the other vessel. For Triton™ X-100, after 1 hour of incubation at 37° C. and agitation at 120 rpm, a 500 U/mL Benzonase® stock solution in 50 mM MgCl$_2$ was added for a final concentration of 10 U/mL in 1 mM MgCl$_2$. After 1 hr of Benzonase® digestion, purification of reovirus from the cell cultures was initiated. For Tween® 20, 20 mM NaPO$_4$ pH 8.0, after 2 hours of incubation at 37° C. and 120 rpm, a 1000 U/mL Benzonase® solution in 50 mM MgCl$_2$ was added for a final concentration of 20 U/mL in 1 mM MgCl$_2$. After 1.5 hr of Benzonase® digestion, purification of reovirus from the cell cultures was initiated.

What is claimed is:

1. A method of producing reovirus, comprising:
   (a) providing a culture of HEK 293 cells which has been infected by reovirus;
   (b) contacting the cells with a first buffer comprising polysorbate 20 and at least 20 mM phosphate and incubating the HEK 293 cells in the presence of the first buffer for a first period of time thereby producing a cell lysate, wherein the incubating occurs at a temperature of about 30° C. to about 40° C. and a pH of about 7.5 to about 8.0, with the proviso that polyethylene glycol p-(1,1,3,3-tetramethylbutyl)-phenyl ether is absent from the first buffer;
   (c) contacting the cell lysate with a second buffer comprising an endonuclease for a second period of time to degrade nucleic acids of the HEK 293 cells;
   (d) removing cell debris by filtration;
   (e) concentrating the filtrate by ultrafiltration and diafiltration;
   (f) purifying the reovirus by a combination of ion exchange and size exclusion chromatography; and
   (g) collecting the reovirus.

2. The method of claim 1, wherein the first buffer comprises 20 mM phosphate.

3. The method of claim 1, wherein the phosphate is sodium phosphate.

4. The method of claim 1, wherein the first buffer comprises 0.5%, 1.0% or 2.0% (v/v) polysorbate 20.

5. The method of claim 1, wherein the first period of time is 60, 120, 180 or 240 minutes.

6. The method of claim 1, wherein the second period of time is 60 minutes, 90 minutes, 120 minutes, 180 minutes, or 240 minutes.

7. The method of claim 1, wherein the endonuclease is contacted with the cell lysate at a concentration of 10 to 20 U/mL.

8. The method of claim 1, wherein contacting the cell lysate with the endonuclease occurs at a temperature of 30° C. to 40° C.

9. The method of claim 1, wherein contacting the cell lysate with the endonuclease occurs at a temperature of 35° C. to 39° C.

10. The method of claim 1, wherein incubating the HEK 293 cells occurs at a temperature of 35° C. to 39° C.

11. The method of claim 1, wherein the second buffer further comprises $MgCl_2$.

12. The method of claim 1, wherein incubating the HEK 293 cells in the presence of the first buffer occurs at a pH of 8.0.

13. The method of claim 1, wherein the HEK 293 cells are grown in suspension.

14. The method of claim 1, wherein the ion exchange is performed using an anion exchanger.

15. The method of claim 1, wherein the ion exchange is performed prior to the size exclusion chromatography.

16. The method of claim 1, wherein a phosphate buffer is used in the ion exchange.

17. The method of claim 16, wherein the phosphate buffer used in the ion exchange comprises 100 mM sodium phosphate.

18. The method of claim 1, wherein a phosphate buffer is used in the size exclusion chromatography.

19. The method of claim 18, wherein the phosphate buffer used in the size exclusion chromatography comprises 10 to 15 mM sodium phosphate.

20. The method of claim 1, wherein the size exclusion chromatography is carried out at a pH of about 7.5 to about 8.0.

21. The method of claim 1, wherein the reovirus is a mammalian reovirus.

22. The method of claim 21, wherein the mammalian reovirus is a human reovirus.

23. The method of claim 22, wherein the human reovirus is a serotype 3 reovirus.

24. The method of claim 23, wherein the serotype 3 reovirus is a Dearing strain reovirus.

25. The method of claim 1, wherein the first buffer comprises 1% (v/v) polysorbate 20.

26. The method of claim 25, wherein the endonuclease is contacted with the cell lysate at a concentration of 20 U/mL.

27. The method of claim 26, wherein the first period of time is at least 120 minutes and the second period of time is at least 90 minutes.

28. The method of claim 3, wherein the first buffer comprises 1% (v/v) polysorbate 20 and 20 mM sodium phosphate, wherein the pH is 8.0, wherein the first period of time is at least 120 minutes and the second period of time is at least 90 minutes, and wherein the endonuclease is contacted with the cell lysate at a concentration of 20 U/mL.

\* \* \* \* \*